(12) United States Patent
Robitzki et al.

(10) Patent No.: US 9,527,894 B2
(45) Date of Patent: Dec. 27, 2016

(54) POLYMUTANT TAU PROTEIN VARIANTS AND THEIR USE FOR RECAPITULATING HUMAN TAUOPATHIES

(75) Inventors: Andrea Robitzki, Viernheim (DE); Heinz-Georg Jahnke, Leipzig (DE); Dana Krinke, Leipzig (DE); Frank Striggow, Gerwisch (DE); Till Mack, Magdeburg (DE)

(73) Assignee: Universitaet Leipzig, Leipzig (DE)

( * ) Notice: Subject to any disclaimer, the term of this patent is extended or adjusted under 35 U.S.C. 154(b) by 0 days.

(21) Appl. No.: 14/114,036

(22) PCT Filed: Apr. 28, 2011

(86) PCT No.: PCT/EP2011/056741
§ 371 (c)(1),
(2), (4) Date: Feb. 5, 2014

(87) PCT Pub. No.: WO2012/146285
PCT Pub. Date: Nov. 1, 2012

(65) Prior Publication Data
US 2014/0162306 A1 Jun. 12, 2014

(51) Int. Cl.
C07K 14/47 (2006.01)

(52) U.S. Cl.
CPC ........... *C07K 14/47* (2013.01); *C07K 14/4711* (2013.01)

(58) Field of Classification Search
None
See application file for complete search history.

(56) References Cited

U.S. PATENT DOCUMENTS

| | | | |
|---|---|---|---|
| 2008/0138811 A1* | 6/2008 | Mack et al. | 435/6 |
| 2008/0201786 A1* | 8/2008 | Rubinstein | 800/3 |
| 2009/0105169 A1* | 4/2009 | Davidson et al. | 514/44 |
| 2009/0247898 A1* | 10/2009 | Robitzki et al. | 600/547 |

OTHER PUBLICATIONS

Lim 2001 "ftdp-17 mutations in tau transgenic mice provoke lysosomal abnormalities and tau filaments in forebrain" Mol Cell Neurosci 18:702-714.*

Vogelsberg-Ragaglia 2000 "Distinct FTDP-17 missense mutations in tau produce tau aggregates and other pathological phenotypes in transfected CHO cells" Mol Biol Cell 11:4093-4104.*
Boeve 2008 "refining ftdp-17: introducing ftdp-17(mapt) and ftdp-17(pgrn)" Arch Neurol 65(4):460-464.*
Santacruz 2005 "tau supression in a neurodegenerative mouse model improves memory function" Science 309:476-481.*
Taes 2010 "tau levels do not influence human als or motor neuron degeneration in the sod1g93a mouse" neurology 74:1687-1693.*
Ko 2005 "Recent advances in experimental modeling of the assembly of tau filaments" Biochimica et Biophysica Acta 1739:125-139.*
F. Lim et al., "FTDP-17 Mutations in tau Transgenic Mice Provoke Lysosomal Abnormalities and Tau Filaments in Forebrain", *Molecular and Cellular Neuroscience*, vol. 18, No. 6, Dec. 1, 2001, pp. 702-714.
V. Vogelsberg-Ragaglia et al., "Distinct FTDP-17 missense mutations in tau produce tau aggregates and other pathological phenotypes in transfected CHO cells", *Molecular Biology of the Cell*, American Society for Cell Biology, US, vol. 11, No. 12, Dec. 1, 2000, pp. 4093-4104.
N. Zilka et al., "Misfolded tau protein and disease modifying pathways in transgenic rodent models of human tauopathies", *Acta Neuropathologica*, Springer, Berlin, Germany, vol. 118, No. 1, Feb. 24, 2009, pp. 71-86.
F. Hernandez et al., "Tauopathies", *CMLS Cellular and Molecular Life Sciences*, Birkhauser-Verlag, BA, vol. 64, No. 17, Jul. 2, 2007, pp. 2219-2233.
R. Brandt et al., "Tau alteration and neuronal degeneration in tauopathies: mechanisms and models", *Biochimica et Biophysica ACTA, Molecular Basis of Disease*, Amsterdam, NL, vol. 1739, No. 2-3, Jan. 3, 2005, pp. 331-354.
J.Z. Wang et al., "Microtubule-associated protein tau in development, degeneration, and protection of neurons", *Progress in Neurobiology*, Pergamon Press, GB, vol. 85, No. 2, Jun. 1, 2008, pp. 148-175.

* cited by examiner

*Primary Examiner* — Adam M Weidner
(74) *Attorney, Agent, or Firm* — Chalin A. Smith; Smith Patent LLC

(57) ABSTRACT

Disclosed herein are methods for identifying an agent for treating or preventing neurogenerative disease and to methods for recapitulating tauopathies using a tau protein that includes at least four different mutations that cause the condition frontotemporal dementia and parkinsonism linked to chromosome 17 (FTDP-17), and to nucleic acids encoding the tau protein.

8 Claims, 4 Drawing Sheets

SRN-003-556

AR-A014418

US 9,527,894 B2

POLYMUTANT TAU PROTEIN VARIANTS AND THEIR USE FOR RECAPITULATING HUMAN TAUOPATHIES

This application corresponds to the national phase of International Application No. PCT/EP2011/056741 filed Apr. 28, 2011, the contents of which are incorporated by reference herein in their entirety.

The instant application contains a Sequence Listing that has been submitted in ASCII format via EFS-Web and is hereby incorporated by reference in its entirety. Said ASCII copy, created on May 11, 2011, is named LNK_140_SequenceListing.txt and is 25,014 bytes in size.

FIELD OF THE INVENTION

The accumulation of proteinaceous aggregates is a pathological hallmark of most if not all chronic dementias characterized by incipient neuronal dysfunction and eventual cell death. In tauopathies, as the name implies, these aggregates take the form of neurofibrillary tangles (NFT) composed essentially of the microtubule-associated protein tau. Though the MAPT gene encoding tau is not genetically linked to Alzheimer's disease (AD), mutations in MAPT cause hereditary frontotemporal dementias (FTD), and missense mutations have also been found in progressive supranuclear palsy, corticobasal degeneration and in conditions that closely resemble Pick's disease, thus providing evidence that disrupting tau homeostasis is sufficient to cause neurodegeneration-driven dementias (reviewed in van Swieten & Spillantini, 2007). In AD, mounting evidence suggests that (wild-type) tau mediates Abeta/amyloid toxicity by hyperphosphorylation and/or redistribution of tau protein (Inner et al. 2010; Zempel et al. 2010) and that reducing tau levels can prevent AD symptoms (Vossel et al. 2010). Tau mutations are known to alter the relative proportion of various tau isoforms and, more importantly, enhance the tendency of tau to adopt an abnormal conformation and, consequently, aggregate into filaments. It is therefore expected that tau-mediated neurodegeneration is caused by a combination of toxic gains of function triggered by abnormalities in tau conformation, as well as from any harmful consequences that may result from the loss of normal tau functions. Unfortunately, the exact mechanisms by which abnormalities in tau conformation initiate, or contribute, to neuronal cell death are not entirely understood. The at best fragmentary understanding of the pathomechanism presents an enormous obstacle for drug development for lack of validated targets for therapeutic intervention. Nevertheless, drug development is pursued in functional models that may recapitulate authentically at least aspects of human tauopathies in vitro and in vivo.

BACKGROUND OF THE INVENTION

Since NFT are the most striking pathological feature in tauopathies, much attention has focused on understanding how the deposition of NFT may cause neurodegeneration, in essence using animal models recapitulating NFT pathology to investigate the mechanism of disease. It has long been postulated that the aggregation of tau into filaments and NFT results in a toxic gain of function. This view has been substantially challenged by observations that neuronal loss and memory impairment can experimentally be cured despite ongoing NFT formation (Santacruz et al. 2005). In some animal models, the tau-mediated loss of neurons does not even require NFT development. Thus, it is assumed that non-filamentous but already aggregated, globular tau intermediates on route to assemble into larger helical filaments may represent the neurotoxic tau species.

Elevated levels of free tau, not bound to microtubules, presumably increases its likelihood to become misfolded, as well as undergo modifications or conformational changes that promote the formation of aggregated small globular oligomers that eventually will assemble into insoluble filaments. Covalent modifications stabilizing conformational changes most likely include phosphorylation since tau protein isolated from AD brain was found to be abnormally high phosphorylated at multiple critical sites ('hyperphosphorylated tau') and it was demonstrated that pseudo-hyperphosphorylation (i.e. pseudo-phosphorylated at multiple sites along the protein) can facilitate abnormal conformation of tau protein (Jeganathan et al. 2008). In this context tau hyperphosphorylation was identified as diagnostic target (WO9311231A1) and different tau related Kinases identified as therapeutic target (WO2007088400A1).

Given that tau is normally a highly soluble protein that does not readily aggregate, this matter has been difficult to assess in experimental models because of the resistance of tau to aggregate within an ideal time-frame for culture studies or within an animal's relatively short lifespan. Because high concentrations of tau are required to promote tau aggregation in experimental models, it is believed that the enhanced ability of tau to form small globular aggregates in the cytoplasm of neurons and glia in human tauopathies may be due to pathological conditions that locally increase the pool of tau available for aggregation. Yet it is unlikely that the amount of tau in various tauopathies is as high as in cell culture and animal models that artificially force massive tau overexpression and, therefore, much caution is needed extrapolating results from such model systems to the human condition.

Further complicating matters is evidence that mouse tau appears to prevent tau aggregation in transgenic mice overexpressing wild-type human tau (htau). Nonetheless, transgenic mice that overexpress high levels of htau isoforms containing aggregation-promoting mutations (e.g. P301L tau) can develop tau pathology even in the presence of endogenous mouse tau. The P301L and P301S mutations are among the first described FTD mutations and show a very early mean onset for FTD in man. Tau transgenic mouse models with expression of these mutants display onset of first signs of tau pathology starting at 2.5 to 5 months (Schindowski et al. 2006). WO 01/53340 A2 discloses mouse models expressing wildtype or tau with one mutation like the named P301L mutation for generating a neurodegenerative disease model as well as tool for drug development. Furthermore a transgenic mouse model with tau cDNA bearing three FTD mutations the tau pathology has been described (Lim et al., 2001).

To accelerate tau aggregation in vitro, polyanionic cofactors or small molecule ligands are often used to facilitate tau aggregation. For example, in a cell culture model overexpressing full length tau, Congo red treatment stimulates the formation of filamentous tau aggregates and decreases cell viability (Bandyopadhyay et al. 2007). These and other results suggest that also in cell culture models tau aggregation causes cell death or, at least, accelerates its onset. However, no cell culture model has been described so far that does not force aggregation of tau by either artificial high concentrations of tau or addition of, at higher doses toxic, compounds in order to facilitate or precipitate aggregation (Ko et al. 2004, Tsukane et al. 2007, Nie et al. 2007). In view of modelling tauopathy disease mechanisms for drug development purposes, both strategies bear a high risk of producing artificial results since the mechanism of degeneration may significantly differ from tau pathology in the AD brain.

SUMMARY OF THE INVENTION

It has been found that cells expressing tau with multiple mutations show signs of neurodegeneration within 24 hours of cell culture. Cells expressing tau proteins with 4 FTDP-17 mutations showed lowered impedance (Example 2/FIG. 5). This was shown for two different tau proteins having different 4× mutations. The effect was even more pronounced for a tau protein having five different FTDP-17 mutations.

In a first aspect, the present invention relates to a tau protein comprising at least four different mutations associated with the condition frontotemporal dementia and parkinsonism linked to chromosome 17 (FTDP-17).

A second aspect of the invention is a nucleic acid encoding the tau protein of the present invention.

A third aspect of the invention is a plasmid or vector comprising the nucleic acid of the present invention.

A fourth aspect of the invention is a cell comprising the nucleic acid or the vector or plasmid of the present invention.

A fifth aspect of the invention is a cell expressing a mutated tau protein, wherein said cell exhibits a decrease in impedance after 24 hours of cell culture.

A sixth aspect of the present invention is a method for identifying an agent for treating or preventing neurogenerative disease, comprising
(a) contacting a test compound with the cell of the present invention; and
(b) determining whether the test substance modulates at least one marker indicative of the neurodegeneration.

A seventh aspect of the invention is the use of the tau protein of the present invention, of the nucleic acid of the present invention, of the vector or plasmid of the present invention, or of the cell of the present invention for screening an agent or agents capable of modulating one or more markers of neurodegeneration.

An eighth aspect of the invention is the use of the tau protein of the present invention, of the nucleic acid of the present invention, of the vector or plasmid of the present invention, or of the cell of the present invention for the development of medicaments for the treatment or prevention of neurodegenerative diseases.

A ninth aspect of the invention is a method for recapitulating a tauopathy, comprising the following steps:
(a) providing the cell of the present invention;
(b) culturing said cell under conditions to allow expression of tau protein having abnormal conformation.

DETAILED DESCRIPTION

Figure 1:
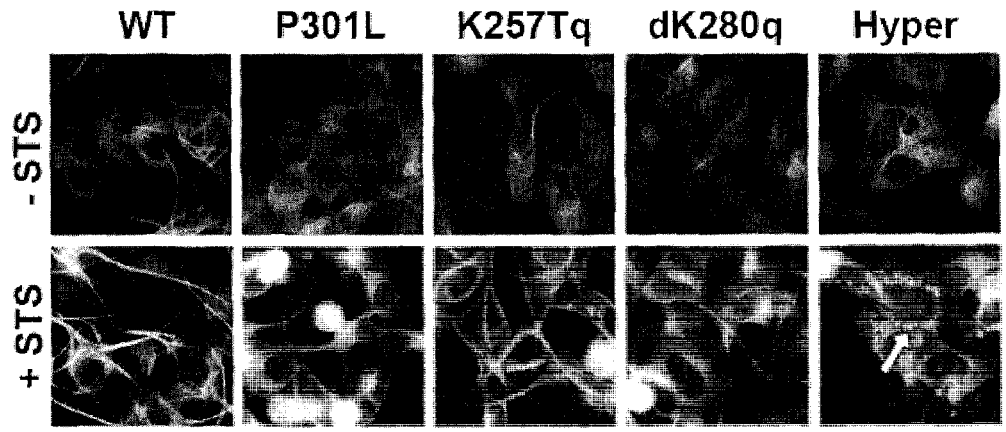
FIG. 1: Abnormal tau aggregation in a hyper-mutated tau expressing cell line. SH-SY5Y neuroblastoma cell lines stably expressing wildtype or mutant tau at a comparable level were used to induce neuronal differentiation by application of 20 nM staurosporine. 48 h of differentiation (+STS) is sufficient for the formation of abnormal tau aggregates in the Hyper-tau expressing cells (arrow).

As used herein and in the appended claims, the singular forms "a", "an" and "the" include plural reference unless the context clearly dictates otherwise. Thus, for example, reference to a "molecule" is a reference to one or more molecules and equivalents thereof known to those skilled in the art, and so forth. The reference to a "cell" includes the reference to a population of cells.

The present invention pertains to a tau protein comprising at least four different mutations selected from the group consisting of mutations associated with the condition frontotemporal dementia and parkinsonism linked to chromosome 17 (FTDP-17).

Tau Protein

The phrase "tau protein", as used herein, denotes a polypeptide having sequence similarity to a wild type tau protein. Preferably, the amino acid sequence of a tau protein has at least 90%, more preferably at least 95% sequence identity to the amino acid sequence as shown in SEQ ID NO:1.The degree of identity of an amino acid sequence to SEQ ID NO 1 may be determined by comparing the amino acid sequence in question and SEQ ID NO 1 using the program "BLAST 2 SEQUENCES (blastp)" (Tatusova et al. (1999) FEMS Microbiol. Lett. 174, 247-250) with the following parameters: Matrix BLOSUM62; Open gap 11 and extension gap 1 penalties; gap x_dropoff50; expect 10.0 word size 3; Filter: none. According to the present invention, the sequence comparison covers at least 200 amino acids, preferably at least 300 amino acids, more preferably at least 350 amino acids, and most preferably at least about 380 amino acids.

Most preferably, the amino acid sequence of a tau protein is selected from the group consisting of SEQ ID NO:1, SEQ ID NO:6 and SEQ ID NO:8. These are the amino acid sequences of tau isoforms 0N4R, 2N4R and 1N4R, respectively.

The tau protein is preferably a human tau protein or a variant thereof. The amino acid sequence of a wild type human tau protein is shown in SEQ ID NO:1. (Homo sapiens microtubule-associated protein tau (MAPT): NM 016834/NP_058518). The amino acid sequences of further human tau isoforms are shown in SEQ ID NO:6 and SEQ ID NO:8. The term "variant" as used herein refers to any polypeptide or protein, in reference to polypeptides and proteins disclosed in the present invention, in which one or more amino acids are added and/or substituted and/or deleted and/or inserted at the N-terminus, and/or the C-terminus, and/or within the native amino acid sequences of the native polypeptides or proteins of the present invention. Furthermore, the term "variant" includes any shorter or longer version of a polypeptide or protein. Variants comprise proteins and polypeptides which can be isolated from nature or be produced by recombinant and/or synthetic means. Native proteins or polypeptides refer to naturally-occurring truncated or secreted forms, naturally occurring variant forms (e.g. splice-variants) and naturally occurring allelic variants. The terms "variant" and "isoform" are used interchangeably herein.

Unless indicated otherwise, the numbering of amino acids in the human tau sequences as used herein refers to the tau isoform having 441 amino acids which is shown in SEQ ID NO:2.

Mutations Associated with FTDP-17

The tau protein of this invention comprises at least four different mutations selected from the group consisting of mutations which are associated with the condition "frontotemporal dementia and parkinsonism linked to chromosome 17" (FTDP-17). FTDP-17 is an autosomal dominant neurodegenerative disorder, which has three cardinal features: behavioral and personality changes, cognitive impairment, and motor symptoms. FTDP-17 was defined during the *International Consensus Conference in Ann Arbor*, Mich., in 1996 (Foster N L, Wilhelmsen K, Sima A A, Jones M Z, D'Amato C J, Gilman S: Frontotemporal dementia and parkinsonism linked to chromosome 17: a consensus conference, Conference Participants, *Ann Neurol* 1997, 41:706-715). This definition is incorporated herein by reference. FTDP-17 is caused by mutations in the tau gene. At least 38 different mutations in the tau gene that are related to FTDP-17 have been identified worldwide.

According to the present invention, mutations associated with FTDP-17 include, but are not limited to: substitution at amino acid position 5, 257, 260, 266, 272, 279, 296, 301, 303, 305, 315, 317, 320, 335, 336, 337, 342, 352, 369, 389, 406 and/or 427; and deletion of amino acid position 280 and/or 296. In particular, mutations associated with FTDP-17 include, but are not limited to the following mutations: R5H, R5L, K257T, I260V, L266V, G272V, N279K, delK280, N296H, N296N, delN296, P301L, P301S, G303V, S305N, L315R, K317M, S320F, G335V, Q336R, V337M, E342V, S352L, K369I, G389R, R406W and/or R427M.

Preferably, the tau protein of the present invention has at least four different mutations, selected from the group consisting of substitution at amino acid position 5, 257, 260, 266, 272, 279, 296, 301, 303, 305, 315, 317, 320, 335, 336, 337, 342, 352, 369, 389, 406 and/or 427; and deletion of amino acid position 280 and/or 296. More preferably, the tau protein of the present invention has at least five different mutations, selected from the group consisting of substitution at amino acid position 5, 257, 260, 266, 272, 279, 296, 301, 303, 305, 315, 317, 320, 335, 336, 337, 342, 352, 369, 389, 406 and/or 427; and deletion of amino acid position 280 and/or 296. In a particular embodiment, the tau protein of the present invention comprises the amino acid sequence as shown in SEQ ID NO:1, except for at least four, preferably at least five different mutations, selected from substitution at amino acid position 5, 257, 260, 266, 272, 279, 296, 301, 303, 305, 315, 317, 320, 335, 336, 337, 342, 352, 369, 389, 406 and/or 427; and deletion of amino acid position 280 and/or 296. In another embodiment, the tau protein of the present invention comprises the amino acid sequence as shown in SEQ ID NO:6, except for at least four, preferably at least five different mutations, selected from substitution at amino acid position 5, 257, 260, 266, 272, 279, 296, 301, 303, 305, 315, 317, 320, 335, 336, 337, 342, 352, 369, 389, 406 and/or 427; and deletion of amino acid position 280 and/or 296. In another embodiment, the tau protein of the present invention comprises the amino acid sequence as shown in SEQ ID NO:8, except for at least four, preferably at least five different mutations, selected from substitution at amino acid position 5, 257, 260, 266, 272, 279, 296, 301, 303, 305, 315, 317, 320, 335, 336, 337, 342, 352, 369, 389, 406 and/or 427; and deletion of amino acid position 280 and/or 296.

More preferably, the tau protein of the present invention has at least four different mutations, selected from the group consisting of [R5H or R5L], K257T, I260V, L266V, G272V, N279K, delK280, [N296H or delN296], [P301L or P301S], G303V, S305N, L315R, K317M, S320F, G335V, Q336R, V337M, E342V, S352L, K369I, G389R, R406W and R427M. More preferably, the tau protein of the present invention has at least five different mutations, selected from the group consisting of [R5H or R5L], K257T, I260V, L266V, G272V, N279K, delK280, [N296H or delN296], [P301L or P301S], G303V, S305N, L315R, K317M, S320F, G335V, Q336R, V337M, E342V, S352L, K369I, G389R, R406W and R427M. In a particular embodiment, the tau protein of the present invention comprises the amino acid sequence as shown in SEQ ID NO:1, except for at least four, preferably at least five different mutations, selected from the group consisting of [R5H or R5L], K257T, I260V, L266V, G272V, N279K, delK280, [N296H or delN296], [P301L or P301S], G303V, S305N, L315R, K317M, S320F, G335V, Q336R, V337M, E342V, S352L, K369I, G389R, R406W and R427M. In another embodiment, the tau protein of the present invention comprises the amino acid sequence as shown in SEQ ID NO:6, except for at least four, preferably at least five different mutations, selected from the group consisting of [R5H or R5L], K257T, I260V, L266V, G272V, N279K, delK280, [N296H or delN296], [P301L or P301S], G303V, S305N, L315R, K317M, S320F, G335V, Q336R, V337M, E342V, S352L, K369I, G389R, R406W and R427M. In another embodiment, the tau protein of the present invention comprises the amino acid sequence as shown in SEQ ID NO:8, except for at least four, preferably at least five different mutations, selected from the group consisting of [R5H or R5L], K257T, I260V, L266V, G272V, N279K, delK280, [N296H or delN296], [P301L or P301S], G303V, S305N, L315R, K317M, S320F, G335V, Q336R, V337M, E342V, S352L, K369I, G389R, R406W and R427M.

In yet another embodiment, the tau protein of the present invention has at least four, preferably at least five different mutations, selected from the group consisting of substitution at amino acid position 5, 257, 272, 279, 301, 305, 337, 389 and/or 406; and deletion of amino acid position 280. In a particular embodiment, the tau protein of the present invention comprises the amino acid sequence as shown in SEQ ID NO:1, except for at least four, preferably at least five different mutations, selected from the group consisting of substitution at amino acid position 5, 257, 272, 279, 301, 305, 337, 389 and/or 406; and deletion of amino acid position 280. In another embodiment, the tau protein of the present invention comprises the amino acid sequence as shown in SEQ ID NO:6, except for at least four, preferably at least five different mutations, selected from the group consisting of substitution at amino acid position 5, 257, 272, 279, 301, 305, 337, 389 and/or 406; and deletion of amino acid position 280. In another embodiment, the tau protein of the present invention comprises the amino acid sequence as shown in SEQ ID NO:8, except for at least four, preferably at least five different mutations, selected from the group consisting of substitution at amino acid position 5, 257, 272, 279, 301, 305, 337, 389 and/or 406; and deletion of amino acid position 280.

According to this embodiment, the tau protein of the present invention may have at least four, preferably at least five different mutations, selected from the group consisting of [R5H or R5L], K257T, G272V, N279K, delK280, [P301L or P301S], S305N, P301L, P301S, V337M, G389R and R406W. In a particular embodiment, the tau protein of the present invention comprises the amino acid sequence as shown in SEQ ID NO:1, except for at least four, preferably at least five different mutations, selected from the group consisting of [R5H or R5L], K257T, G272V, N279K, delK280, [P301L or P301], S305N, P301L, P301S, V337M, G389R and R406W. In another embodiment, the tau protein of the present invention comprises the amino acid sequence as shown in SEQ ID NO:6, except for at least four, preferably at least five different mutations, selected from the group consisting of [R5H or R5L], K257T, G272V, N279K, delK280, [P301L or P301S], S305N, P301L, P301S, V337M, G389R and R406W. In another embodiment, the tau protein of the present invention comprises the amino acid sequence as shown in SEQ ID NO:8, except for at least four, preferably at least five different mutations, selected from the group consisting of [R5H or R5L], K257T, G272V, N279K, delK280, [P301L or P301S], S305N, P301L, P301S, V337M, G389R and R406W.

More preferably, the tau protein of the present invention has at least four different mutations, selected from the group consisting of substitution at amino acid position 257, 301, 337, and/or 406; and deletion of amino acid position 280. In a particular embodiment, the tau protein of the present invention comprises the amino acid sequence as shown in SEQ ID NO:1, except for at least four different mutations, selected from the group consisting of substitution at amino acid position 257, 301, 337, and/or 406; and deletion of amino acid position 280. In another embodiment, the tau protein of the present invention comprises the amino acid sequence as shown in SEQ ID NO:6, except for at least four different mutations, selected from the group consisting of substitution at amino acid position 257, 301, 337, and/or 406; and deletion of amino acid position 280. In another embodiment, the tau protein of the present invention comprises the amino acid sequence as shown in SEQ ID NO:8, except for at least four different mutations, selected from the group consisting of substitution at amino acid position 257, 301, 337, and/or 406; and deletion of amino acid position 280. According to another embodiment, the tau protein of the present invention has at least four different mutations, selected from the group consisting of K257T, delK280, [P301L or P301S], V337M and R406W. In a particular embodiment, the tau protein of the present invention comprises the amino acid sequence as shown in SEQ ID NO:1, 6 or 8, except for at least four different mutations, selected from the group consisting of K257T, delK280, [P301L or P301S], V337M and R406W.

Most preferably, the tau protein of the present invention has at least the following five different mutations: Substitution at amino acid positions 257, 301, 337 and 406, and deletion of amino acid position 280. In a particular embodiment, the tau protein of the present invention comprises the amino acid sequence as shown in SEQ ID NO:1, 6 or 8, except for amino acid substitutions at amino acid positions 257, 301, 337 and 406, and deletion of amino acid position 280. According to another preferred embodiment, the tau protein of the present invention has at least the five different mutations K257T, delK280, [P301L or P301S], V337M and R406W, e.g. K257T, delK280, P301L, V337M and R406W. According to this embodiment, the tau protein of the present invention may comprise the amino acid sequence as shown in SEQ ID NO:1, except for the mutations K257T, delK280, [P301L or P301S], V337M and R406W; e.g. except for K257T, delK280, P301L, V337M and R406W. The tau protein of this embodiment may comprise the amino acid sequence as shown in SEQ ID NO:3, which is the most preferred embodiment. In another embodiment, the tau protein of the present invention may comprise the amino acid sequence as shown in SEQ ID NO:6, except for the mutations K257T, delK280, [P301L or P301S], V337M and R406W; e.g. except for K257T, delK280, P301L, V337M and R406W. In another embodiment, the tau protein of the present invention may comprise the amino acid sequence as shown in SEQ ID NO:8, except for the mutations K257T, delK280, [P301L or P301S], V337M and R406W; e.g. except for K257T, delK280, P301L, V337M and R406W.

Nucleic Acids, Vectors and Plasmids

The invention further relates to nucleic acids encoding the proteins of the invention described herein.

The term "nucleic acid" generally refers to any polyribonucleotide or polydeoxyribonucleotide that may be unmodified RNA or DNA or modified RNA or DNA. The polynucleotide may be single- or double-stranded DNA, single or double-stranded RNA. It will be appreciated that a variety of modifications may be made to DNA and RNA that serve many useful purposes known to those of skill in the art. The term "nucleic acid" as it is employed herein embraces such chemically, enzymatically or metabolically modified forms of polynucleotides, as well as the chemical forms of DNA and RNA characteristic of viruses and cells, including, for example, simple and complex cells.

Nucleic acid sequences which encode the appropriate proteins or polypeptides can be readily prepared by the skilled person using the information and references contained herein and techniques known in the art (for example, see Sambrook et al., "Molecular Cloning, A Laboratory Manual, $3^{rd}$ ed. 2001, CSH Press, Cold Spring Harbor, N.Y., and Ausubel et al., Short Protocols in Molecular Biology, John Wiley and Sons, 1992). These techniques include the use of the polymerase chain reaction (PCR) to amplify samples of the relevant nucleic acid, e.g. from genomic sources, chemical synthesis, and/or preparation of cDNA sequences. DNA encoding e.g. tau may be generated and used in any suitable way known to those of skilled in the art, including by taking encoding DNA, identifying suitable restriction enzyme recognition sites either side of the portion to be expressed, and cutting out said portion from the DNA. Mutation can be introduced into tau-encoding sequences, e.g. using site directed mutagenesis.

cDNA sequences encoding tau proteins are known in the art (e.g. Gen-ID NM016834). The skilled person can therefore easily manipulate the DNA by known techniques to provide polynucleotides that encode the desired tau protein or variant thereof. The DNA sequence of wild type tau is shown in SEQ ID NO:4.

Further aspects of the invention are vectors and plasmids containing a nucleic acid of the invention.

A "vector" is a replicon, such as plasmid, phage, cosmid, or virus to which another polynucleotide segment may be operably inserted so as to bring about the replication or expression of the segment. The vector may particularly be a plasmid, a cosmid, a virus or a bacteriophage used conventionally in genetic engineering that comprise a polynucleotide encoding tau protein or a variant thereof. Methods which are well known to those skilled in the art can be used to construct recombinant viral vectors; see, for example, the techniques described in Sambrook et al., "Molecular Cloning, A Laboratory Manual, $3^{rd}$ ed. 2001, CSH Press, Cold Spring Harbor, N.Y. and Ausubel et al., Current Protocols in Molecular Biology, Green Publishing Associates and Wiley Interscience, N.Y. (1989).

The term "recombinant" means, for example, that a polynucleotide sequence is made by an artificial combination of two otherwise separated segments of sequence, e.g., by chemical synthesis or by the manipulation of isolated polynucleotides by genetic engineering techniques Expression vectors will contain a promoter which is operably linked to the protein-encoding nucleic acid sequence of interest, so as to direct mRNA synthesis.

Promoters recognized by a variety of potential host cells are well known. "Operably linked" means joined as part of the same nucleic acid molecule, suitably positioned and oriented for transcription to be initiated from the promoter. DNA operably linked to a promoter is "under transcriptional control" of the promoter. Transcription from vectors in mammalian host cells may be controlled, for example, by promoters obtained from the genomes of viruses such as Simian Virus 40 (SV40), from heterologous mammalian promoters, e.g. the actin promoter or an immunoglobulin promoter, and from heat-shock promoters, provided such promoters, are compatible with the host cell systems. Expression vectors used in eukaryotic host cells will also contain sequences necessary for the termination of transcription and for stabilizing the mRNA.

The promoter used herein may be constitutive or inducible. In a preferred embodiment expression control sequences specify induced expression of the polypeptide of the invention. Transcription of the messenger RNA encoding the polypeptide of the invention is induced upon addition or withdrawal of an external signal, such as a small chemical like tetracycline or a hormone like Ecdysone. The external signal can also be an increase or decrease in temperature or ionizing radiation. Also, inducible expression can be brought about by inducible translation initiation of the messenger RNA or a system in which mRNA stability is controlled in an inducible fashion. Examples of expression control sequences allowing induction of polypeptide production are disclosed in the following publications: the Tet-off/Tet-on system, for example described by Gossen and Bujard (1992) Proc Natl Acad Sci USA, 15; 89 (12): 5547-51; or by Gossen et al. (1995) Science, June 23; 268 (5218): 1766-9; or by Kistner et al. (1996) Proc Natl Acad Sci USA 93: 10933-10938, but also the expression control system based on Cre-recombinase based methods. A further inducible expression system, for use in both cell culture and transgenic animals is based on the insect hormone Ecdysone, for example described by Hoppe et al. (2000) Mol Ther, 1: 159-164; or by No et al. (1996) Proc Natl Acad Sci USA, 93: 3346-3351. Another inducible expression system is the GAL4 system (Ornitz et al. (1991) Proc Natl Acad Sci USA, February 1; 88 (3): 698-702) which allows conditional expression at 26-29 degrees, or also a Rapamycin based conditional expression system (Ho et al. (1996) Nature, August 29; 382 (6594): 822-6; and Pollock et al. (2000) Proc Natl Acad Sci USA, November 21; 97 (24): 13221-6). A temperature-sensitive expression system is based on a Sindbis virus expression cassette (Boorsma et al. (2000) Nat Biotechnol, April; 18 (4): 429-32) and predominantly suitable for controlled expression in cell culture systems.

Expression vectors of the invention may also contain one or more selection genes. Typical selection genes encode proteins that confer resistance to antibiotics or other toxins (e.g. ampicillin, neomycin, methotrexate, or tetracycline), complement auxotrophic deficiencies, or supply critical nutrients not available from complex media. Examples of selectable markers for mammalian cells include DHFR and thymidine kinase. Thus a typical of the present invention may include an origin of replication, one or more protein sequence(s) operably linked to a constitutive or inducible promoter as appropriate, a transcription termination sequence, and a marker gene.

The vectors and plasmids containing the polynucleotide described herein can be transferred into the host cell by well-known techniques, which vary depending on the type of cellular host (see infra).

Cells, Transfection and Transduction

A further aspect of the invention is a cell comprising the nucleic acid or the vector or plasmid described herein. The cell is preferably an isolated cell, i.e. it is not in its natural environment such as a tissue. More preferably, the cell is a cell culture cell in a culture medium.

The cell is preferably a living cell which can be cultured in cell culture. Preferably, the cell is a eukaryotic cell, more preferably it is a mammalian cell. Mammalian cell lines available in the art for expression of a heterologous polypeptide include fibroblast 3T3 cells, HeLa cells, baby hamster kidney cells, COS cells, Chinese hamster ovary cells, human liver cells (Hep G2); and many others. In a particular embodiment, the cell of the invention is a neuronal cell or a precursor thereof. "Neuronal cells" as used herein, are cells that express the marker protein microtubule-associated protein-2 (MAP-2). They may further express the marker proteins neurofilament and/or calbindin. Suitable neuronal cells include, but are not limited to primary neuronal cells preferably of the central nervous system (CNS), pluripotent stem cells (ES and iPS) derived neurons and transdifferentiated neurons. Such cells are described, e.g., in Otto et al. Journal of Neuroscience Methods 128 (2003) 173-181 (primary neuronal cells); Pankratz et al., 2007, Stem Cells 25(6): 1511-1520 (ES cells); Hu et al., 2010, PNAS 107(9): 4335-4340 (iPS cells); and Vierbuchen et al., 2010, Nature 463, 1035-1041 (transdifferentiated neurons).

The precursor cell of a neuronal cell can be converted into a cell having neuronal phenotype by exposing the cell to a differentiation stimulus. Usually, differentiation into a neuronal phenotype can be induced by adding a differentiation agent to the precursor cells in cell culture. Suitable precursor cells include, but are not limited to, SH-SY5Y cells (Agholme et al., 2010, Journal of Alzheimer's Disease 20: 1069-1082), Neuro2A cells (Trembley et al., 2010, Journal of Neuroscience Methods 186: 60-67), NG108-15 cells (Zhong et al. Journal of Neurochemistry 68(6): 2291-2299; ATCC HB-12317), IMR32 cells (ATCC CCL-127) and PC-12 cells (Schimmelpfenig et al., 2004, Journal of Neuroscience Methods 139: 299-306). Suitable differentiation agents include staurosporine, retinoic acid, trichostatin A, differentiation promoting media formulation e.g. Neurobasal (A)+B27-Supplement, N2-Supplement and combinations thereof.

The nucleic acid, vector or plasmid of the invention can be introduced into the cells using techniques known to those skilled in the art. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. The calcium treatment employing calcium chloride, as described in Sambrook et al., supra, or electroporation is generally used for prokaryotes or other cells that contain substantial cell-wall barriers.

As used herein, the term "transduction," is used to describe the delivery and introduction of polynucleotide to eukaryotic cells using viral mediated delivery systems, such as, adenoviral, AAV, retroviral, or plasmid delivery gene transfer methods. These methods are known to those of skill in the art, with the exact compositions and execution being apparent in light of the present disclosure.

As used herein, the term "transfection" is used to describe the delivery and introduction of polynucleotide to a cell using non-viral mediated means, these methods include, e.g., calcium phosphate- or dextran sulfate-mediated transfection; electroporation; glass projectile targeting; and the like. These methods are known to those of skill in the art, with the exact compositions and execution being apparent in light of the present disclosure.

The transfection or transduction may be stable or transient. Preferably the transfection or transduction is transient. This generally refers to transient expression of the DNA construct introduced into the cells.

Host cells transfected or transduced with expression or cloning vectors described herein may be cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in "Mammalian Cell Biotechnology: a Practical Approach", M. Butler, ed. JRL Press, (1991) and Sambrook et al, supra.

Cells Having Reduced Impedance

An additional aspect of the invention is a cell expressing a mutated tau protein, wherein said cell exhibits reduced electric impedance. The cell is preferably an isolated cell, i.e. it is not in its natural environment such as a tissue. More preferably, the cell is a cell culture cell in a culture medium.

The general cell types of this aspect of the invention are the same as described hereinabove, and cell culturing can be carried out according to established methods. Gene expression can be confirmed, for example, by Northern blotting to quantitate the transcription of mRNA, or in situ hybridization, using an appropriately labeled probe, based on the sequence of the recombinant nucleic acid introduced into the cell. Gene expression, alternatively, may be measured by immunological methods such as immunohistochemical staining of cells to quantitate directly the expression of gene product. Antibodies useful for immunohistochemical staining and/or assay of sample fluids may be either monoclonal or polyclonal.

Expression of the mutated tau protein is preferably detected using antibodies directed against tau. Alternatively, the mutated tau protein may be fused to a label, e.g. a heterologous peptide sequence (FLAG tag, HA tag etc.) which can be detected by methods known in the art. In one embodiment, the mutated tau protein is fused to a heterologous amino acid sequence, e.g. EGFP, FLAG tag, or Strep tag. This allows to specifically detect the mutated tau in a Western blot using anti-tau antibodies. According to this embodiment, the mutated tau can be distinguished from the endogenous wild type tau due to its different size on a Western blot.

Preferably, the mutated tau is not strongly overexpressed in the cell. In one embodiment, the amount of mutated tau in the cell is preferably less than the ten-fold amount of wild type tau expressed in the same cell or in a control cell, e.g. a non-transfected cell of the same cell type. More preferably, the amount of mutated tau in the cell is less than the five-fold amount of wild type tau expressed in the same cell or in a control cell, e.g. a non-transfected cell of the same cell type. Still more preferably, the amount of mutated tau in the cell is less than the two-fold amount of wild type tau expressed in the same cell or in a control cell, e.g. a non-transfected cell of the same cell type. Most preferably, the amount of mutated tau in the cell is about 75% to about 150%, or about 75% to about 125%, of the amount of wild type tau expressed in the same cell or in a control cell, e.g. a non-transfected cell of the same cell type. The level of expression is preferably determined by Western blotting and subsequent detection of mutated tau and endogenous wild-type tau using anti-tau antibodies, and optionally anti-tag antibodies. In a particular embodiment, the desired level of expression is obtained by an inducible expression system, such as the known Tet-on-off system, see supra.

Tau protein having abnormal conformation can be detected by using specific antibodies. Examples of such antibodies include the monoclonal antibodies MC-1 (Jicha, G. A., Bowser, R., Kazam, I. G., Davies, P., 1997. J. Neurosci. Res. 48 (2), 128-132) and Alz50 (Davis et al., 1994, Journal of Neuroscience Research 39(5): 589-594). In a specific embodiment, the "cell expressing a mutated tau protein" is a cell in which a protein can be detected using the monoclonal antibody MC-1, preferably using the experimental conditions described with respect to FIG. 2 infra.

Impedance spectroscopy—also known as cellular dielectric spectroscopy (CDS) or electric impedance spectroscopy (EIS)—can be used to measure frequency dependent alterations of passive electrical properties of single cells by applying defined alternate currents and/or voltages. The bio-impedance of single cells can be measured with a working electrode and a counter electrode. Different cellular parameters such as the capacitance and resistance of the cell membranes as well as intracellular membranes of organelles, the resistance of the extracellular medium and intrinsic cytoplasm, the extracellular matrix and the contact between cell and electrode contribute to the overall cellular impedance. To analyze alterations of impedance of living cells, an alternate voltage is applied to a biological sample. Depending on the dielectric properties of sub-cellular compartments and molecules the applied current can flow from an active working electrode through the cells whereby the remaining current is collected by a counter electrode. Depending on the frequency of the applied voltage, alterations of certain cellular compartments can be identified.

For the present invention, impedance spectroscopy is preferably carried out as described in Jahnke et al. (Lab Chip, 2009, 9, 1422-1428), the disclosure if which is incorporated herein by reference. The device for measuring the impedance of cells may be one as described in EP 2103933 A1.

The cell according to this aspect has an electric impedance which is reduced relative to a control cell. The control cell is a cell identical to the cell expressing the mutated tau, except that it does not express the mutated tau. For example, the control cell is of the same cell type as the cell of the invention but does not contain a recombinant nucleic acid encoding said mutated tau. In a preferred embodiment, the control cell is an untransfected cell or wild type cell of the same cell type as the cell of the present invention. In another embodiment, the control cell has been transfected with a mock vector, e.g. a plasmid without coding sequence. In yet another embodiment, the control cell is a cell transfected with a vector comprising a nucleic acid sequence encoding wildtype tau, e.g. tau represented by SEQ ID NO:1, 6 or 8. In the latter embodiment, the expression level in the control cell of the wild-type tau is substantially the same as that of the mutated tau in the cell of the present invention.

Figure 4:
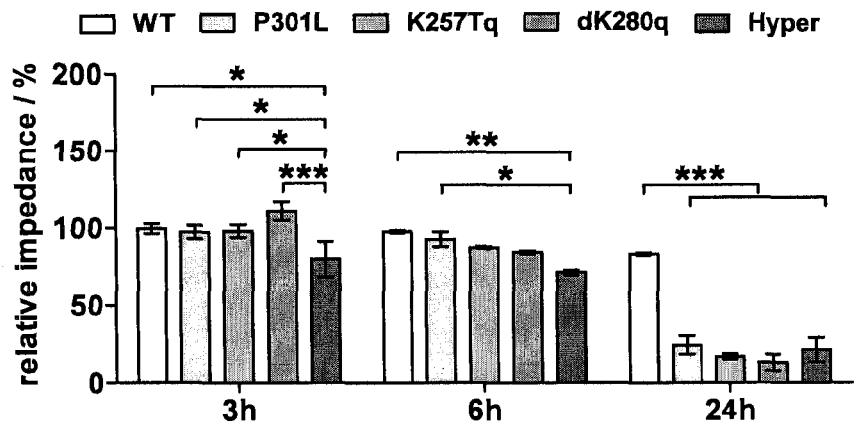
FIG. 4: Impedimetric detection of consequences by okadaic acid induced artificial hyperphosphorylation. While the incubation with 25 nM okadaic acid initially shows a Hyper-tau mutant specific degenerative effect at 3 h and 6 h the unspecific toxic side effects of okadaic acid resulted in massive cell damage in all tau mutants after 24 h. (n=3, 2D-ANOVA, Bonferoni post-hoc test, *$p<0.05$, $p<0.01$, *$p<0.001$)

In the cell of the invention the electrical impedance is preferably reduced by at least 5%, more preferably by at least 10%, most preferably by at least 20%, relative to the (untransfected) control cell not expressing mutated tau, determined under the conditions used in Example 2/FIG. 4.

The cell of the invention has a reduced electric impedance in the absence of okadaic acid. In another embodiment, the cell of the invention has a reduced electric impedance in the absence of phosphatase inhibitors, e.g., okadaic acid. Preferably, the cell of the invention has a reduced electric impedance in the absence of okadaic acid and Congo Red. In another preferred embodiment, the cell of the invention has a reduced electric impedance in the absence of phosphatase inhibitors (e.g. okadaic acid) and Congo Red. More preferably, the cell of the invention has a reduced electric impedance in the absence of okadaic acid, Congo Red and formaldehyde. In another more preferred embodiment, the cell of the invention has a reduced electric impedance in the absence of phosphatase inhibitors (e.g. okadaic acid), Congo Red and formaldehyde. Still more preferably, the cell of the invention has a reduced electric impedance in the absence of okadaic acid, Congo Red, formaldehyde and any other toxic substance. Most preferably, the cell of the invention has a reduced electric impedance in the absence of phosphatase inhibitors (e.g. okadaic acid), Congo Red, formaldehyde and any other toxic substance. In yet another embodiment, the cell of the invention has a reduced electric impedance in the absence of phosphatase inhibitors (e.g. okadaic acid), Congo Red, formaldehyde, polyanionic substances (e.g. heparin, polyglutamate) and any other toxic substance.

In a preferred embodiment, the cell is a neuronal cell expressing mutated tau which is detectable by the antibody MC-1, and exhibiting an electric impedance reduced by at least 10% relative to a control cell not expressing mutated tau, determined under the conditions used in Example 2.

In another preferred embodiment, the cell of the invention is a neuronal cell or precursor cell thereof, characterized by the following features:
the cell expresses a mutated tau protein;
after addition of a differentiation agent to the cell in cell culture, the cell shows a reduction in electric impedance within 24 hours after addition of the differentiation agent, wherein said reduction is by at least 10% relative to a control cell not expressing mutated tau, determined under the conditions used in Example 2/Figure.

Preferably, the reduction in electric impedance occurs within 18 hours, more preferably within 12 hours, most preferably within 6 hours after addition of the differentiation agent. It is also preferred that no toxic agent is present in the culture medium of the cell (e.g. okadaic acid, Congo Red, formaldehyde etc.).

Methods And Uses of the Invention

In one aspect, the invention relates to a method for identifying an agent for treating or preventing a tauopathy, comprising
(a) contacting a test compound with the cell of the present invention; and
(b) determining whether the test substance modulates at least one marker indicative of the neurodegeneration.

Neurodegenerative diseases or disorders in accordance the present invention comprise Alzheimer's disease, Parkinson's disease, Huntington's disease, amyotrophic lateral sclerosis, prion diseases, Pick's disease, fronto-temporal dementia, progressive nuclear palsy, corticobasal degeneration, cerebro-vascular dementia, multiple system atrophy, and mild-cognitive impairment. Further conditions involving neurodegenerative processes are, for instance, ischemic stroke, age-related macular degeneration, narcolepsy, motor neuron diseases, nerve injury and repair, and multiple sclerosis.

Preferably, the neurodegenerative disease is a taupathy. "Tauopathies" are disorders and diseases, characterized by the presence of neuronal tau aggregation, in particular the presence of neurofilbrillary tangles. Typical tauopathies are Alzheimer's disease and other neurodegenerative disorders such as FTDP-17, Pick's disease, progressive supranuclear palsy, amyotrophic lateral sclerosis/Parkinsonism-dementia complex of Guam and corticobasal degeneration.

Preferably, the neurodegenerative disease is selected from the group consisting of Alzheimer's disease, Parkinson's disease, multiple sclerosis, amyotrophic lateral sclerosis, huntington's disease, tauopathies and prion diseases. Most preferably, the neurodegenerative disease is Alzheimer's disease.

The phrase "marker" as used herein refers to any parameter that indicates the onset or presence of a neurodegenerative disease on a cellular level. Suitable markers include the presence of neurofibrillary tangles, a decrease in impedance, phosphorylation of tau, dendritic/axonal dystrophy, axonal degeneration, β-amyloid production, synaptic dystrophy, microtubule and overall cytosceleton function/integrity/-based transport/distribution, proteasomal function, cellular morphology, cellular adhesion, signal transduction, receptor distribution/function, and all other cellular functions which may be affected. Preferred markers include the presence of neurofibrillary tangles, decrease in impedance, phosphorylation of tau, dendritic/axonal dystrophy, axonal degeneration, β-amyloid production and synaptic dystrophy, as well as cellular morphology.

A test compound "modulates" a marker indicative of a neurodegenerative disease when it is capable of changing or altering the level and/or the activity of the marker. Said modulation may be an increase or a decrease in the level and/or the activity of the marker. For instance, said modulation may be an increase or decrease in phosphorylation of tau, dendritic/axonal dystrophy, axonal degeneration, synaptic dystrophy and/or the amount of neurofibrillary tangles present.

The formation of neurofibrillary tangles in cells may be determined by the Gallyas silver impregnation method followed by light/electron microscopy or other appropriate methods (Braak, H. and Braak, E. (1995) *Neurobiol Aging* 16, 271-8; discussion 278-84). One such other appropriate method comprises the utilization of conformation-dependent antibodies that are capable of recognizing and discriminating the tau molecule in the context of neurofibrillary tangles from tau molecules existing in other states of aggregation and that can be detected, for instance, by fluorescence microscopy and/or fluorescence resonance energy transfer (FRET) technology. The formation of neurofibrillary tangles could also be detected by the use of other optical methodologies such as fluorescence polarisation spectroscopy, fluorescence correlation spectroscopy, fluorescence cross-correlation spectroscopy, fluorescence intensity distribution analysis, fluorescence lifetime measurements, fluorescence anisotropy measurements, or combinations thereof. For instance, an assay to monitor and quantify the formation and aggregation of paired helical filaments in solution has been described by Friedhoff et al. (1998, Biochemistry, 37: 10223-30). In a preferred embodiment, said conformation-dependent antibodies are optically labeled, preferably fluorescently labeled.

According to another embodiment, the method of the invention comprises determining the phosphorylation at one or more of the phosphorylation sites Ser198, Ser199, Ser202, T231, S235, S396, S404, S409, S413 and S422. Phosphorylation of disease-specific phosphorylation sites confirms that tau-transfected cells are in a process of AD-like degeneration: Phosphorylation of Ser202/Thr205 (known as the AT8 site) has been identified as a diagnostic marker epitope, i.e. it is indicative of early stages of neurodegeneration, preceding tangle formation and neuronal loss in Alzheimer's disease. In another embodiment, the method of the invention comprises determining the phosphorylation at Ser202 and/or Thr205.

The extent of phosphorylation of tau at the respective epitopes may be determined using suitable antibodies which specifically recognize phosphoepitopes of tau or non-phosphorylated regions of tau. Currently available antibodies have been described, for instance, in Johnson, G. V. and Hartigan, J. A. (1999) *J Alzheimers Dis* 1, 329-51 and are commercially available. Quantification of Tau phosphoepitopes may be done by Western blotting followed by densitometrical analysis of the signals according to standard procedures.

Dendritic or axonal dystrophy/degeneration can be determined by biochemical determination, visual inspection and/or tissue section (staining) labelling employing suitable markers (etc. antibodies detecting the heavy isoform of neurofilament as detailed in Mack et al. (2001) *Nat Neurosci* 4, 1199-206). Morphologically, Wallerian degeneration of axons has been described in detail in Beirowski et al. (2005) *BMC Neurosci* 6, 6.

Synaptic dystrophy can be determined by biochemical determination, visual inspection and/or tissue section labelling (staining) employing suitable markers such as synapsin or synaptophysin (Rutten et al., 2005, *Am J Pathol* 167, 161-73).

In a specific embodiment, the method further comprises the step of co-treatment of the cells with β-amyloid precursor protein (β-APP) or a fragment or derivative or variant thereof (see supra). Alternatively, the β-amyloid precursor protein (β-APP) or a fragment or derivative or variant thereof may be expressed in the cell, preferably under the control of an inducible system, as described above. This embodiment may comprise the step of transfecting or transducing said cells with a recombinant vector comprising a polynucleotide encoding β-amyloid precursor protein or a fragment or derivative or variant thereof. The preferred fragment is the β-amyloid peptide $A\beta_{1-42}$. The β-amyloid peptide is derived from a larger Type I membrane spanning protein, β-APP, which has several alternatively spliced transcripts. The amino acid sequences of β-APP and $A\beta_{1-42}$ are described in Kang J. et al., 1987; Knauer M. F et al., 1992; Homo sapiens APP (Gen-ID): NM 201414. These sequences are incorporated herein by reference.

The term "fragment" as used herein is meant to comprise e.g. an alternatively spliced, or truncated, or otherwise cleaved transcription product or translation product. The term "derivative" as used herein refers to a mutant, or an RNA-edited, or a chemically modified, or otherwise altered transcription product, or to a mutant, or chemically modified, or otherwise altered translation product. For instance, a "derivative" may be generated by processes such as altered phosphorylation, or glycosylation, or, acetylation, or lipidation, or by altered signal peptide cleavage or other types of maturation cleavage. These processes may occur post-translationally.

The step of determining whether the test substance modulates at least one marker indicative of the neurodegenerative disease may comprise the following steps: (i) measuring the marker in the cell or in the cell culture which has been contacted with the test substance; (ii) measuring the marker in a cell or cell culture which has not been contacted with the test substance (control cell or control cell culture); and optionally (iii) comparing the level or activity of marker determined in (i) and (ii).

In another embodiment, the step of determining whether the test substance modulates at least one marker indicative of the neurodegenerative disease may comprise the following steps: (i) measuring the marker in the cell or in the cell culture which has been contacted with the test substance; (ii) measuring the marker in a control cell (or control cell culture) which does not express mutated tau and which has not been contacted with the test substance; and optionally (iii) comparing the level or activity of marker determined in (i) and (ii).

The method may comprise the step of selecting or identifying as an agent for treating or preventing neurodegenerative disease a test compound which is capable of decreasing the level or activity of the marker indicative of the neurodegenerative disease. The test compound may be selected if it is capable of significantly decreasing the level or activity of the marker. Preferably, if the marker can be measured in a quantitative manner, the test compound is selected if it is capable of decreasing the level or activity of the marker by at least 10%, preferably by at least 20%, more preferably by at least 30%, even more preferably by at least 40%, most preferably by at least 50% as compared to the control cell or control cell culture.

In a particular embodiment, the test compound may be selected if it is capable of significantly increasing the electric impedance of the cell of the invention. Preferably, the test compound is selected if it is capable of increasing the electric impedance of the cell of the invention by at least 5%, preferably by at least 10%, more preferably by at least 15%, even more preferably by at least 20%, most preferably by at least 25% as compared to the control cell or control cell culture which has not been contacted with the test compound.

In another particular embodiment, the test compound is selected if it is capable of increasing the electric impedance of the cell of the invention such that the electric impedance of the cell of the invention differs by less than 10%, more preferably by less than 5% from that of a control cell which does not express mutated tau.

The method may further comprise the step of measuring the viability of the cell of the invention. This may be done by using methods such as: visual inspection under a microscope; staining using vital dyes stains and immunohistochemical reagents specific for cell types or moieties present in normal and injured brain; reaction with antibodies to neurofilaments, glial fibrillary acidic protein, S100, microtubule associated proteins, and synaptic proteins; biochemical assessment of metabolic activity; measurement of total or specific protein content; assessment of cellular function; and assessment of neural activity.

The viability/integrity of the cell or cell culture may be assessed at the initiation of each experiment in order to demonstrate the health of the cells as well as to provide a measure of the amount of viable cells present in the pre-treated cell culture.

Test Compound

Compounds that are assayed in the above method can be randomly selected or rationally selected or designed. As used herein, a compound is said to be randomly selected when the compound is chosen randomly without considering the structure of other identified active compounds. An example of randomly selected compounds is the use a chemical library, a peptide combinatorial library, a growth broth of an organism, or a plant extract.

As used herein, a compound is said to be rationally selected or designed when the compound is chosen on a nonrandom basis. Rational selection can be based on the target of action or the structure of previously identified active compounds. Specifically, compounds can be rationally selected or rationally designed by utilizing the structure of compounds that are presently being investigated for use in treating Alzheimer's disease.

The test compounds can be, as examples, peptides, small molecules, and vitamin derivatives, as well as carbohydrates. The test compounds may be nucleic acids, natural or synthetic peptides or protein complexes, or fusion proteins. They may also be antibodies, organic or inorganic molecules or compositions, drugs and any combinations of any of said agents above. They may be used for testing, for diagnostic or for therapeutic purposes. A skilled artisan can readily recognize that there is no limit as to the structural nature of the test compounds to be used in accordance with the present invention.

Application of Test Substance

At the commencement of an experiment, a cell culture comprising cells according to the present invention is typically provided. The culture media can either have a test compound present prior to the introduction of the cells, or a test compound can be added to the media after the cells have been placed in the culture dish. In general, a test substance will be first dissolved in appropriate vehicle, such as, but not limited to, DMSO, water, physiological saline, or media, to make a stock solution and then diluted into the media. A vehicle control test may be included when the present invention is used.

Preferably, a range of doses is tested. The range tested initially may be informed by prior knowledge of the effects of the test compound or closely related substances on purified proteins, cells in culture, or toxicity in other test systems. In the absence of such knowledge, the dose range is preferably from about 1 nM to about 100 µM. A skilled artisan can readily develop a testing range for any particular compound or series of compounds.

The test compound is typically applied to the cell or cell culture for about one hour to about 21 days, preferably from about 3 hours to about 7 days, more preferably from about 6 hours to about 3 days, most preferably from about 18 hours to about 2 days, e.g. about 24 hours. In the case of long term application, fresh media containing test compound can be applied periodically; more frequently if rapid loss of test compound due to chemical conversion or to metabolism is suspected. In a particular embodiment, the cells of the invention are contacted with a differentiation agent as described above. The differentiation agent may be added to the cells prior to exposing the cells to the test substance (e.g. 24 or 48 hours before), or the differentiation agent may be added simultaneously with the test substance, and the cells are then cultured further. These embodiments apply to the methods described above mutatis mutandis.

An another aspect, the invention relates to the use of the tau protein of the present invention, of the nucleic acid of the present invention, of the vector or plasmid of the present invention, or of the cell of the present invention for screening an agent or agents capable of modulating one or more markers of neurodegeneration.

In yet another aspect, the invention relates to the use of the tau protein of the present invention, of the nucleic acid of the present invention, of the vector or plasmid of the present invention, or of the cell of the present invention for the development of medicaments for the treatment or prevention of neurodegenerative diseases.

In yet another aspect, the invention relates to a method for recapitulating a tauopathy, comprising the following steps:
(a) providing the cell of the present invention;
(b) culturing said cell under conditions to allow expression of tau protein having abnormal conformation.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

The following materials and methods were used in the examples described hereinbelow:

Generation of SH-SY5Y Cell Lines Stably Expressing EGFP-Fused Tau

The cDNA from human wildtype tau (0N4), was amplified by PCR from isolated human neuronal cell mRNA. During PCR, a Bg/II site was inserted at the 5' and a SalI site at the 3'-end of the tau gene. The PCR product was cloned into the pEGFP-C1 vector C-terminal to the EGFP coding sequence. For lentiviral transduction the EGFP-tau wildtype coding sequence was amplified by PCR with BamHI (5') and XhoI (3') restrictions sites and cloned into a lentiviral transduction vector. The EGFP-tau (poly)mutants were obtained by site-directed mutagenesis (QuickChange Lightning, Stratagene). For lentiviral virus particle production the Lentiviral TOPO Expression Kit (Invitrogen) was used. SH-SY5Y cell lines were transduced by lentiviral particles and cells stably expressing the EGFp-tau construct were selected by blasticidin.

Cell Culture and Cell Treatment

Human neuroblastoma SH-SY5Y cells were grown in DMEM medium, supplemented with 15% fetal bovine serum (FBS), non-essential amino acids, glutamax and penicillin/streptomycine (Invitrogen). Differentiation of SH-SY5Y cells was induced by incubation of the SH-SY5Y cells with 20 nM stauropsprin (Sigma-Aldrich) for 48 hours. For the appropriate experiments differentiated cells were treated with okadaic acid (Sigma-Aldrich) in a concentration of 25 nM or in case of reference compound testing with SRN-003-556 and AR-A014418, respectively.

Immunocytochemistry

Cells were grown on coverslips and fixed with 4% formaldehyde at room temperature for 30 min, followed by permeabilization with 0.1% Triton X-100. Cells were incubated with anti-acetylated tau antibody(Abcam, 1:1000) for two hours at room temperature. After washing three times with PBS, cells were incubated with Cy3-linked secondary antibody (Dianova, 1:100) for 1.5 hours. Nuclei were stained with DAPI (Sigma-Aldrich). Confocal images were taken with a Nikon Eclipse C1 LSM microscope.

Western Blot Analysis

Cells were harvested and protease as well as phosphatase inhibitor cocktail (Sigma-Aldrich) was added. Proteins were extracted by sonification (Hielscher GmbH) and protein concentration was determined using the Roti-Nanoquant Assay (Carl-Roth GmbH). Laemmli sample buffer was added to 60 µg cell lysate. Samples were separated on 10% SDS-polyacrylamide gel and electro transferred onto polyvinylidene fluoride membranes and subsequently immuno-labeled with anti-MC1 specific antibody (Peter Davis Department of Pathology, Albert Einstein College of Medicine, 1:100) at 4° C. over night. Secondary antibody was horseradish peroxidase conjugated (Dianova, 1:5000). Specific protein signals were detected using Chemiluminescence Detection Kit (MobiTec) and ChemiDoc-XRS (Bio-Rad).

Impedance Measurements

Cells were cultured on self-developed 96-well arrays comprising a gold electrode at the culture surface. The SH-SY5Y cells were differentiated for 48 hours on the 96-well arrays. Impedance spectra were recorded with a self developed multiplexer unit for the 96-well arrays and an impedance Analyser Agilent 4294A (Agilent Technologies) with an alternating voltage of 10 mV with frequencies from 500 Hz to 5 MHz (0 mV bias between electrodes). For each experiment at least five wells were measured in replicate. All impedance magnitude spectra were analysed with a self-developed software IDAT (Impedance Data Analysing Tool). IDAT calculates the impedance of cell-covered electrodes relative to electrodes without cells (relative impedance: $(|Z|_{covered} - |Z|_{cell-free})/|Z|_{cell-free} \times 100\%$) and determine the and select the frequency where impedance change caused by the cell layer is maximum (for SH-SY5Y cells on 96-well array at about 100 kHz). Relative impedance over time was further normalised to time point zero (100%) to make different wells and experiments comparable and allow comprehensive statistical analysis. Experiments were repeated at least three times.

Example 1

In a first example multiple combinations of polymutant tau variants were produced and tested as transgenes in a human neuroblastoma cell line. For a better overview and comparison a single mutant tau (P301L), a 4× polymutant $\text{tau}_{\Delta K280/P301L/V337M/R406W}$ (dK280q) as well as the 4× polymutant $\text{tau}_{K257T/P301L/V337M/R406W}$ (K257Tq) and a 5× polymutant $\text{tau}_{K257T/\Delta K280/P301L/V337M/R406W}$ also referred to as hyper mutant tau (Hyper) are shown. In order to assure comparable levels of tau variant transgene expression, all constructs were expressed using the same lentiviral expression system. Transgenic cell lines were rapidly generated after viral infection and selection of transduced cells that had stably integrated the tau variant transgene into their genome.

Unexpectedly, it was found that the induction of differentiation (20 nM staurosporine) lead to the formation of abnormal tau aggregates exclusively in the Hyper-tau cell line (FIG. 1, arrow) without the addition of toxic cofactors like okadaic acid (Jahnke et al. 2009) or the use of massive overexpression of the tau transgene.

Figure 2:
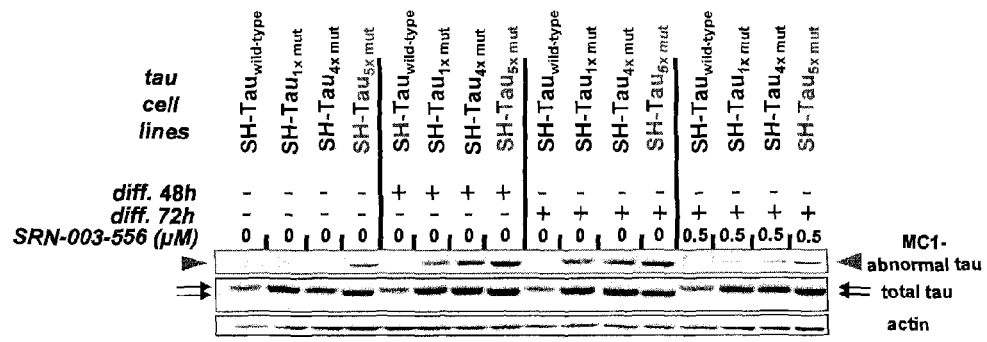
FIG. 2: Abnormal tau conformation in polymutant tau cell lines. Poly-mutant tau variants were developed and, using those variants, poly-mutant neuroblastoma cell lines were produced. In those cell lines tau adopting an abnormal/pathological conformation under physiological conditions was observed (MC1 abnormal tau). A 5× mutated tau gene variant (SH-Tau$_{5\times\ mut}$) demonstrated a particular high tendency for an abnormal conformation as detected by the MC1 marker (red arrowhead) despite similar expression levels compared to wild-type or single mutant protein. Corroborating recent results that phosphorylation may stabilize abnormal conformation the amount of MC1-positive tau species could be decreased by treating the cells with a tau kinase inhibitor (SRN-003-556). Thus, polymutant tau protein is present in an Alzheimer-like phosphorylation state in differentiated neuroblastoma cells and kinase inhibition decreases tau missfolding and may also suppress subsequent aggregation.

A more detailed analysis of the cell lines on the molecular level revealed the accumulation of misfolded tau protein under various conditions (FIG. 2). The results showed that, in undifferentiated neuroblastoma cell lines, only the Hyper-tau variant bearing 5 FTD mutations gave rise to abnormally conformed, misfolded tau species detected by the conformation-dependent antibody MC1 (FIG. 2; upper panel). This 5× mutant variant was therefore referred to as a 'hyper-mutated' tau variant since it led to the presence of tau protein in an abnormal MC1-conformation without additional stimuli or treatments. After differentiation of the cells for 48 or 72 hours, respectively, a massive increase of misfolded tau species in all but the wild-type variant cell lines was observed, the 5× mutant variant displaying peak levels of MC1-conformation tau isoforms.

Interestingly, pathologically misfolded tau species also reveal themselves by migrating slightly faster than species in a physiological conformation (i.e. wild-type control tau) during PAGE electrophoresis, presumably due to a more compact conformation (FIG. 2; middle panel showing total tau; most compact and loose conformational isoforms marked by arrows). This finding is also perfectly in line with results from Jeganathan et al. (2008) suggesting that pathological tau from AD brains recognised by the conformation-dependent antibody MC1 persists in a compact 'paperclip' conformation which favours aggregation but opposes microtubule stabilization.

Figure 3:
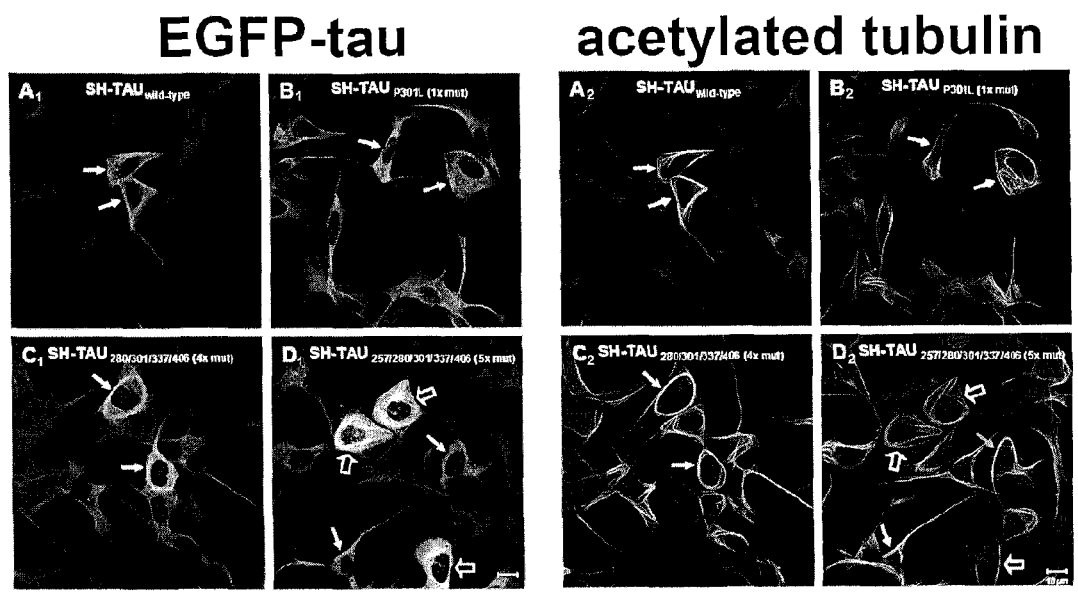
FIG. 3: Microtubule network pathology in 5× polymutant tau neuroblastoma cells after differentiation into neuronal phenotype. Indicated MAPT gene variants were transduced using retroviral vectors into the human neuroblastoma cell line SH-SY5Y and stable expressing cell lines were selected. Differentiated cells were analyzed for transgene expression (EGFP-tau, $A_1$-$D_1$) and changes in the microtubule network detected by an antibody against acetylated tubulin ($A_2$-$D_2$), a marker for stable microtubules. Double-label fluorescence shows a filamentous pattern of stabile microtubules in infected cells and local colacalization of microtubules with transgenic tau (A-D, white arrows), as would be expected of a microtubule-associated protein. In contrast, in a subpopulation of cells (D, open arrows) transduced with the 5× polymutant variant stable microtubules were absent. Concomitantly, whose cells display high levels of EGFP-tagged tau transgene and appear to have lost their processes. A collapse of the (stable) microtubule network is expected to cause a disruption of the microtubule-dependent transport and a slow atrophy of the cell culminating in death of affected cells.

Furthermore, the 'hyper-mutated' tau variant was also unique with respect to microtubule integrity. Mutant tau not only has a high tendency to aggregate, and by doing so may loose its physiological function, but on top of that clearly seems to carry out a toxic gain of function resulting in specific neurotoxicity (not affecting glial cells). However, the exact nature of this toxic gain of function is not yet understood. When the stability of the microtubule network in three mutated tau and a wild-type tau control cell line was compared (FIG. 3), the inventors observed thick bundles of stable microtubules in cells expressing eGFP-tagged tau transgenes (white arrows). In those cells, acetylated tubulin as a marker for post-translational modified, stabile microtubules strongly colocalized with transgenic tau giving rise to a bright yellow filamentous pattern In contrast, in a subpopulation of differentiated neuronal-type cells bearing the 5× mutant MAPT gene variant (FIG. 3, D) an apparent loss of stabile microtubules was observed (open arrows). In those cells, despite marked expression of the tau transgene, colocalized microtubules were absent. At any given time-point, in a fraction of neuronal cells tau toxicity-dependent break-down of microtubules may lead to a progressive loss of the microtubule network. Polymutant tau variants may rise the percentage of affected cells or considerably enhance microtubule destruction enabling a screen for effective microtubule pathology-modulators.

Aggregated tau oligomers (as large as in FIG. 1 or even smaller precursors) may constitute the toxic tau species attacking the microtubule network and, ultimately, may be responsible for interruption of vital microtubule-dependent transport function slowly atrophying the cell. Moreover, the results are corroborated by growing evidence that microtubule-based axonal and dendritic transport and, thus, synapse/spine maintenance is primarily affected by tau-dependent degeneration in AD (see for example Zempel et al. 2010).

Example 2

To demonstrate the unique performance of the Hyper-tau mutant cell line impedance spectroscopy was used as a sensitive label-free real-time monitoring technique, described in detail in Jahnke et al. 2009. In a first step the inventors used the toxic phosphatase-inhibitor okadaic acid that is widely used in AD-related in vitro assays for the hyperphosphorylation of the tau protein (FIG. 4).

Given that okadaic is commonly used for artificial induction of tau hyperphosphorylation in in vitro experiments under non-physiological conditions, the inventors were able to detect impedimetrically an initial Hyper-tau mutant specific degenerative effect after 3 and 6 hours, respectively. With increasing incubation time toxic side effects of okadaic acid leads to overall cell toxicity in all tau mutant cell lines resulting in a strong decrease of impedance.

Figure 5:
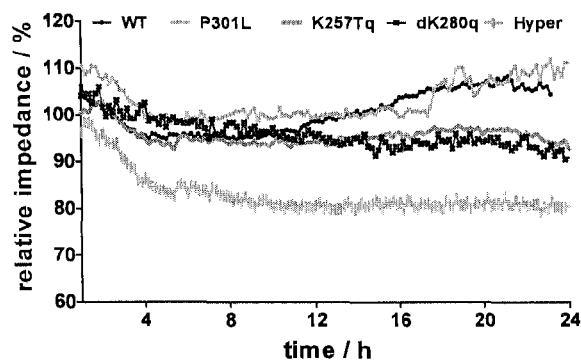
FIG. 5: Differentiation induces neurodegeneration in poly-mutant tau expressing SH-SY5Y cells. Differentiation of SH-SY5Y cells were induced by 48 h incubation with 20 nM staurosporine. Afterwards the cells were impedimetrically monitored for 24 h. While wildtype tau and P301L-tau expressing cells showed no decrease of impedance, K257q and dK280q-tau cells showed lowered impedance. Strikingly, the Hyper-tau expressing cells showed a more significant impedance decrease as a result of neurodegeneration. (n=4, 2D-ANOVA, Bonferoni post-hoc test, *$p<0.05$, **$p<0.01$)
Figure 5:
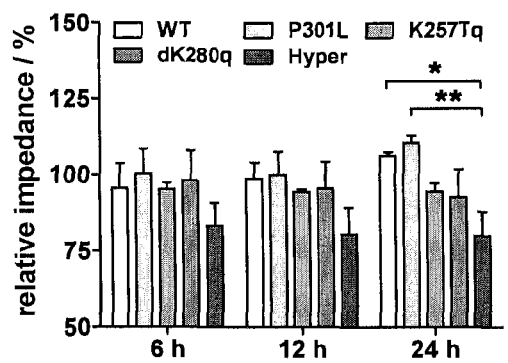

To overcome the limitations of using artificial induction of pathology and thereby focusing to specific but not fully validated targets e.g. hyperphosphorylation and/or aggregation in vitro, the inventors took advantage of the poly-mutant tau, especially the Hyper-tau mutant that show neuropathological phenotype only by induction of neuronal differentiation (see FIG. 1). Therefore the wildtype and poly-mutant tau expressing cells were differentiated for 48 hours followed by impedimetric monitoring for 24 hours (FIG. 5). The mean values from 3 experiments with 4-6 replicates reveals that the single mutant P301L tau expressing cells show the same impedimetric characteristic like the wildtype tau expressing cells. While the 4× polymutant K257Tq and dK280q already show lower impedance values after 20 hours compared to the wildtype and P301L tau expressing cells, the Hyper-tau expressing cells show a still more substantial decrease of relative impedance caused by induced neurodegeneration.

Example 3

The unique effects of the Hyper-mutant tau could be used in a functional tau pathology in vitro screening assay for identification and efficiency quantification of potential active pharmaceutical ingredients. Taking the significant difference between the physiological condition (wildtype tau expressing cells) and the pathological condition (Hyper-tau expressing cells) that can be monitored via impedance spectroscopy, the efficiency of compounds to attenuate the pathological cellular degeneration can be quantitatively determined.

Figure 6:
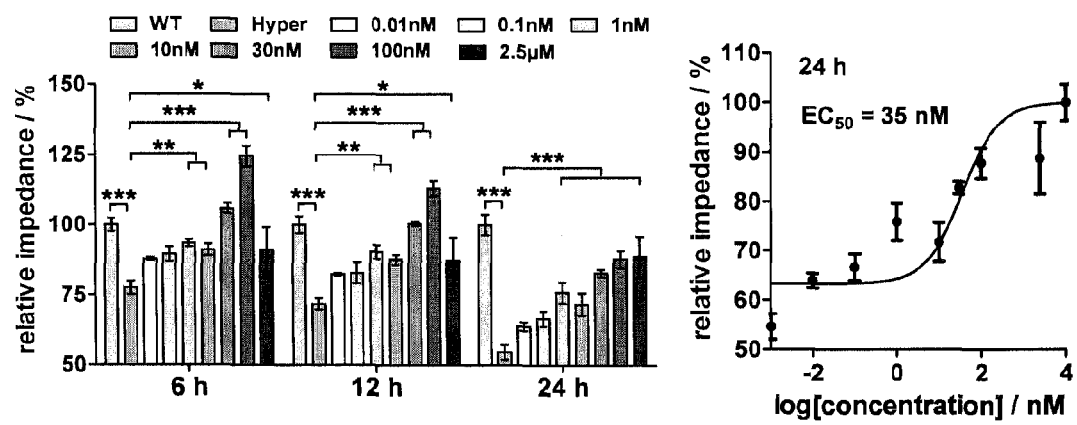
FIG. 6: Use of Hyper-tau cells for quantitative detection of compound efficiency. Taking the developed Hyper-tau cells, where pathology was induced by differentiation (20 nM staurosporine for 48 h) in comparison to the wildtype tau expressing cells (physiological condition) the efficiency of potential active pharmaceutical ingredients could be quantified. The effect of two reference compounds, in detail the kinase inhibitor SRN-003-556 and AR-A014418 were used to demonstrate screening capability of the Hyper-tau based functional tau pathology screening assay. While SRN-003-556 show a significant reduction of Hyper-tau induced pathology, AR-A014418 shows no significant therapeutic effect. Observable therapeutic effects can be quantified, as demonstrated by $EC_{50}$ determination exemplarily for SRN-003-556 at 24 h (values are normalized to WT, n=4, all groups compared to Hyper, 2D-ANOVA, Bonferoni post-hoc test, *p<0.05, p<0.01, *p<0.001)
Figure 6:
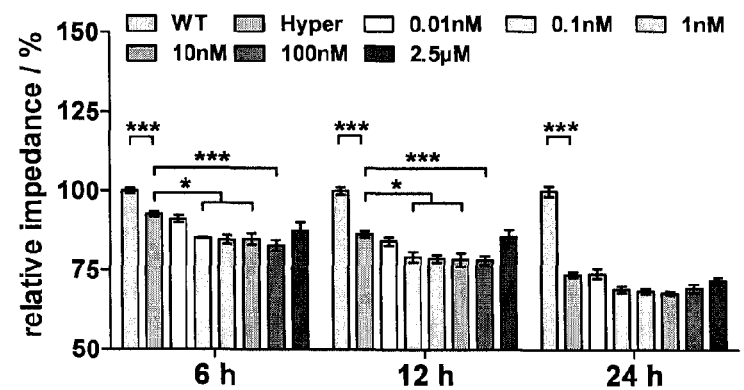

Exemplarily the inventors used two kinase inhibitors to demonstrate the capabilities of the Hyper-tau based screening assay (FIG. 6). In detail SRN-003-556, a developed lead compound with moderate specificity to ERK2, and AR-A014418, a specific GSK3R-inhibitor were tested. Both inhibitors showed a therapeutic effect within tau pathology in vitro assays that are based on artificial hyperphosphorylation using toxic compounds like okadaic acid (LeCorre et al. 2006, Selenica et al. 2007, Jahnke—unpublished data). But only SRN-003-556 showed a therapeutic effect in a tauopathy mouse model while AR-A014418 does not (LeCorre et al. 2006, Selenica et al. 2007).

Using the impedance spectroscopy based functional tau pathology in vitro screening assay the inventors were able to quantitatively determine the therapeutic effect of SRN-003-556 with an $EC_{50}$ value of 35 nM at 24 hours. In contrast AR-A014418 showed no therapeutic effect.

These results show the advantage of the novel polymutant tau based in vitro model that is not predetermined to hypothetic targets like kinase mediated hyperphosphorylation (achieved by using toxic compounds like okadaic acid), aggregation promoter and refolding/degradation promoters as well as oligomer or fibrillar tau structures that often generate false positive hits. Furthermore the impedimetric monitoring gives the opportunity to detect potential side effects like neurotrophic effects (FIG. 6, SRN-003-556, 6 h and 12 h, 100 nM) or toxic effects (AR-A014418, 6 h and 12 h, 0.1 nM-100 nM). Using the polymutant tau variants in functional tau pathology in vitro screening assays will highly improve target identification and validation as well as prediction of potential active pharmaceutical ingredients efficiency.

REFERENCES

Bandyopadhyay, B., G. Li, H. Yin, and J. Kuret. 2007. Tau aggregation and toxicity in a cell culture model of tauopathy. *J Biol Chem.* 282:16454-64.

Ittner, L. M., Y. D. Ke, F. Delerue, M. Bi, A. Gladbach, J. van Eersel, H. Wolfing, B. C. Chieng, M. J. Christie, I. A. Napier, A. Eckert, M. Staufenbiel, E. Hardeman, and J. Gotz. 2010.

Dendritic function of tau mediates amyloid-beta toxicity in Alzheimer's disease mouse models. *Cell.* 142:387-97.

Jahnke, H. G., Rothermel, A., Sternberger, I., Mack, T. G., Kurz, R. G., Panke, O., Striggow, F., Robitzki, A. A. 2009. An impedimetric microelectrode-based array sensor for label-free detection of tau hyperphosphorylation in human cells. *LabChip.* 21:9(10)

Jeganathan, S., A. Hascher, S. Chinnathambi, J. Biernat, E. M. Mandelkow, and E. Mandelkow. 2008. Proline-directed pseudo-phosphorylation at AT8 and PHF1 epitopes induces a compaction of the paperclip folding of Tau and generates a pathological (MC-1) conformation. *J Biol Chem.* 283:32066-76.

Kang, J., Lemaire, H. G., Unterbeck, A., Salbaum, J. M., Masters, C. L., Grzeschik, K. H., Multhaup, G., Beyreuther, K. and Muller-Hill, B. (1987). The precursor of Alzheimer's disease amyloid A4 protein resembles a cell-surface receptor. Nature 325, 733-6.

Knauer, M. F., Soreghan, B., Burdick, D., Kosmoski, J. and Glabe, C. G. (1992). Intracellular accumulation and resistance to degradation of the Alzheimer amyloid A4/beta protein. *Proc Natl Acad Sci USA* 89, 7437-41.

Ko, L. W., T. Rush, N. Sahara, J. S. Kersh, C. Easson, M. Deture, W. L. Lin, Y. D. Connor, and S. H. Yen. 2004. Assembly of filamentous tau aggregates in human neuronal cells. *J Alzheimers Dis.* 6:605-22; discussion 673-81.

Lim, F., F. Hernandez, J. J. Lucas, P. Gomez-Ramos, M. A. Moran, and J. Avila. 2001. FTDP-17 mutations in tau transgenic mice provoke lysosomal abnormalities and Tau filaments in forebrain. *Mol Cell Neurosci.* 18:702-14.

LeCorre, S., Klafki, H. W., Plesnila, N., Hübinger, G., Obermeier, A., Sahagu, H., Monse, B., Seneci, P., Lewis, J., Eriksen, J., Zehr, C., Yue, M., McGowan, E., Dickson, D. W., Hutton, M. and Roder, H. M. 2006. An inhibitor of tau hyperphosphorylation prevents severe motor impairments in tau transgenic mice. PNAS. 103:25; 9673-78

Nie, C. L., Y. Wei, X. Chen, Y. Y. Liu, W. Dui, Y. Liu, M. C. Davies, S. J. Tendler, and R. G. He. 2007. Formaldehyde at low concentration induces protein tau into globular amyloid-like aggregates in vitro and in vivo. *PLoS One.* 2:e629.

Rosenmann, H., N. Grigoriadis, H. Eldar-Levy, A. Avital, L. Rozenstein, O. Touloumi, L. Behar, T. Ben-Hur, Y. Avraham, E. Berry, M. Segal, I. Ginzburg, and O. Abramsky. 2008. A novel transgenic mouse expressing double mutant tau driven by its natural promoter exhibits tauopathy characteristics. *Exp Neurol.* 212:71-84.

Santacruz, K., J. Lewis, T. Spires, J. Paulson, L. Kotilinek, M. Ingelsson, A. Guimaraes, M. DeTure, M. Ramsden, E. McGowan, C. Forster, M. Yue, J. Orne, C. Janus, A. Mariash, M. Kuskowski, B. Hyman, M. Hutton, and K. H. Ashe. 2005. Tau suppression in a neurodegenerative mouse model improves memory function. *Science.* 309: 476-81.

Selenica, M. L., Jensen, H. S., Larsen, A. K., Pedersen, M. L., Helboe L, Leist, M., Lotharius, J. 2007. Efficacy of small-molecule glycogen synthase kinase-3 inhibitors in the postnatal rat model of tau hyperphosphorylation. *Br J. Pharmacol.* 152:6,969-79

Schindowski, K., A. Bretteville, K. Leroy, S. Begard, J. P. Brion, M. Hamdane, and L. Buee. 2006. Alzheimer's disease-like tau neuropathology leads to memory deficits and loss of functional synapses in a novel mutated tau transgenic mouse without any motor deficits. *Am J. Pathol.* 169:599-616.

Tsukane, M., C. Yoshizaki, and T. Yamauchi. 2007. Development and specific induction of apoptosis of cultured cell models overexpressing human tau during neural differentiation: Implication in Alzheimer's disease. *Anal Biochem.* 360:114-22.

van Swieten, J., and M. G. Spillantini. 2007. Hereditary frontotemporal dementia caused by Tau gene mutations. *Brain Pathol.* 17:63-73.

Vossel, K. A., K. Zhang, J. Brodbeck, A. C. Daub, P. Sharma, S. Finkbeiner, B. Cui, and L. Mucke. 2010. Tau Reduction Prevents A{beta}-Induced Defects in Axonal Transport. *Science.*

Zempel, H., E. Thies, E. Mandelkow, and E. M. Mandelkow. 2010. Abeta oligomers cause localized Ca(2+) elevation, missorting of endogenous Tau into dendrites, Tau phosphorylation, and destruction of microtubules and spines. *J. Neurosci.* 30:11938-50.

Amino Acid and Nucleotide Sequences Shown in the Sequence Listing:

SEQ ID NO:1 shows the amino acid sequence of a wild type human tau protein (Homo sapiens microtubule-associated protein tau (MAPT): NM 016834/NP_058518).

SEQ ID NO:2 shows the amino acid sequence of the human the tau isoform having 441 amino acids.

SEQ ID NO:3 shows the amino acid sequence of a modified human tau protein having five FTDP-17 mutations relative to the wild type sequence.

SEQ ID NO:4 shows a nucleotide sequence encoding SEQ ID NO:1.

SEQ ID NO:5 shows a nucleotide sequence encoding SEQ ID NO:3.

SEQ ID NO:6 and 7 show the amino acid and nucleotide sequences, respectively, of another isoform of human tau protein, with the following details:

| | |
|---|---|
| LOCUS | NM_005910 1326 bp mRNA linear PRI 03-APR-2011 |
| DEFINITION | *Homo sapiens* microtubule-associated protein tau (MAPT), transcript variant 2, mRNA. |
| ACCESSION | NM_005910 REGION 323..1648 |
| VERSION | NM_005910.5 GI294862262 |

SEQ ID NO:8 and 9 show the amino acid and nucleotide sequences, respectively, of yet another isoform of human tau protein, with the following details:

| | |
|---|---|
| LOCUS | NM_001123067 1239 bp mRNA linear PRI 03-APR-2011 |
| DEFINITION | *Homo sapiens* microtubule-associated protein tau (MAPT), transcript variant 5, mRNA. |
| ACCESSION | NM_001123067 REGION: 323..1561 |

The invention claimed is:

1. A method for identifying an agent for treating the condition frontotemporal dementia and parkinsonism linked to chromosome 17 (FTDP-17), said method comprising the steps of:
   a. contacting a test substance with a cell expressing a tau protein having (i) at least the mutations P301L, V337M, and R406W and (ii) either or both of the K280 deletion and the K257T mutation, wherein the amino acid numbering refers to SEQ ID NO: 2, wherein said cell exhibits a decrease in impedance after 24 hours of cell culture; and
   b. determining whether the test substance modulates at least one marker indicative of neurodegeneration.

2. The method of claim 1, wherein said cell has the phenotype of a neuronal cell.

3. The method of claim 1, wherein the impedance exhibited by said cell is decreased by at least 10% relative to a control cell not expressing mutated tau, determined after 24 hours of cell culture.

4. The method of claim 1, wherein the marker indicative of the neurodegeneration is selected from the group consisting of cell impedance, neurofibrillary tangles, phosphorylation of tau, dendritic/axonal dystrophy, axonal degeneration, axonal transport and synaptic dystrophy.

5. The method of claim 1, wherein step (b) comprises (i) measuring the impedance of the cell in the absence of the test substance, (ii) measuring the impedance of the cell in the presence of the test substance, and (iii) comparing the impedance measured in (i) with the impedance measured in (ii).

6. The method of claim 1, wherein step (b) comprises (i) measuring the marker in the cell or in the cell culture which has been contacted with the test substance; (ii) measuring the marker in a control cell (or control cell culture) which does not express mutated tau and which has not been contacted with the test substance; and (iii) comparing the level or activity of marker determined in (i) and (ii).

7. The method of claim 1, comprising
   i. culturing the cell in a culture medium;
   ii. adding the test substance to the culture medium and further culturing the cell in the presence of the test substance for a period of time which is at least 1 hour;
   iii. optionally measuring said marker prior to step (ii);
   iv. measuring said marker at least once after step (ii).

8. The method of claim 7, wherein said period of time is at least 12 hours.

* * * * *

SEQUENCE LISTING

<160> NUMBER OF SEQ ID NOS: 9

<210> SEQ ID NO 1
<211> LENGTH: 383
<212> TYPE: PRT
<213> ORGANISM: homo sapiens

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Ala Pro Lys Thr Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380
```

<210> SEQ ID NO 2
<211> LENGTH: 441
<212> TYPE: PRT

<213> ORGANISM: homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

-continued

Gly Asp Thr Ser Pro Arg His Leu Ser Asn Val Ser Thr Gly Ser
            405                 410                 415

Ile Asp Met Val Asp Ser Pro Gln Leu Ala Thr Leu Ala Asp Glu Val
        420                 425                 430

Ser Ala Ser Leu Ala Lys Gln Gly Leu
        435                 440

<210> SEQ ID NO 3
<211> LENGTH: 382
<212> TYPE: PRT
<213> ORGANISM: Artificial Sequence
<220> FEATURE:
<223> OTHER INFORMATION: human tau having five mutations

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Thr Ser Lys Ile Gly Ser Thr Glu Asn Leu
        195                 200                 205

Lys His Gln Pro Gly Gly Gly Lys Val Gln Ile Ile Asn Lys Leu Asp
    210                 215                 220

Leu Ser Asn Val Gln Ser Lys Cys Gly Ser Lys Asp Asn Ile Lys His
225                 230                 235                 240

Val Leu Gly Gly Gly Ser Val Gln Ile Val Tyr Lys Pro Val Asp Leu
                245                 250                 255

Ser Lys Val Thr Ser Lys Cys Gly Ser Leu Gly Asn Ile His His Lys
            260                 265                 270

Pro Gly Gly Gly Gln Met Glu Val Lys Ser Glu Lys Leu Asp Phe Lys
        275                 280                 285

Asp Arg Val Gln Ser Lys Ile Gly Ser Leu Asp Asn Ile Thr His Val
    290                 295                 300

Pro Gly Gly Gly Asn Lys Lys Ile Glu Thr His Lys Leu Thr Phe Arg
305                 310                 315                 320

```
Glu Asn Ala Lys Ala Lys Thr Asp His Gly Ala Glu Ile Val Tyr Lys
                325                 330                 335

Ser Pro Val Val Ser Gly Asp Thr Ser Pro Trp His Leu Ser Asn Val
            340                 345                 350

Ser Ser Thr Gly Ser Ile Asp Met Val Asp Ser Pro Gln Leu Ala Thr
        355                 360                 365

Leu Ala Asp Glu Val Ser Ala Ser Leu Ala Lys Gln Gly Leu
    370                 375                 380

<210> SEQ ID NO 4
<211> LENGTH: 1152
<212> TYPE: DNA
<213> ORGANISM: Homo sapiens

<400> SEQUENCE: 4
atggctgagc cccgccagga gttcgaagtg atggaagatc acgctgggac gtacggttg      60 ggggacagga aagatcaggg gggctacacc atgcaccaag accaagaggg tgacacggac     120
gctggcctga agctgaaga gcaggcatt ggagacaccc ccagcctgga agacgaagct       180
gctggtcacg tgacccaagc tcgcatggtc agtaaaagca agacgggac tggaagcgat      240 gacaaaaaag ccaaggggc tgatggtaaa acgaagatcg ccacaccgcg gggagcagcc     300
cctccaggcc agaagggcca ggccaacgcc accaggattc agcaaaaac cccgcccgct     360 ccaaagacac acccagctc tggtgaacct ccaaaatcag ggatcgcag cggctacagc      420 agccccggct ccccaggcac tcccggcagc cgctcccgca cccgtccct tccaaccca      480 cccaccccggg agcccaagaa ggtggcagtg gtccgtactc acccaagtc gccgtcttcc   540 gccaagagcc gcctgcagac agccccgtg cccatgccag acctgaagaa tgtcaagtcc    600
aagatcggct ccactgagaa cctgaagcac agccgggag cgggaaggt gcagataatt      660 aataagaagc tggatcttag caacgtccag tccaagtgtg gctcaaagga taatatcaaa    720
cacgtcccgg gaggcggcag tgtgcaaata gtctacaaac cagttgaacct gagcaaggtg   780 acctccaagt gtggctcatt aggcaacatc catcataaac caggaggtgg ccaggtggaa    840
gtaaaatctg agaagcttga cttcaaggac agagtccagt cgaagattgg gtccctggac    900
aatatcaccc acgtccctgg cggaggaaat aaaaagattg aaacccacaa gctgaccttc    960
cgcgagaacg ccaaagccaa gacagaccac ggggcggaga tcgtgtacaa gtcgccagtg   1020
gtgtctgggg acacgtctcc acggcatctc agcaatgtct cctccaccgg cagcatcgac   1080
atggtagact cgccccagct cgccacgcta gctgacgagg tgtctgcctc cctggccaag   1140
cagggtttgt ga                                                        1152

<210> SEQ ID NO 5
<211> LENGTH: 1149
<212> TYPE: DNA
<213> ORGANISM: homo sapiens

<400> SEQUENCE: 5
atggctgagc cccgccagga gttcgaagtg atggaagatc acgctgggac gtacggttg      60 ggggacagga aagatcaggg gggctacacc atgcaccaag accaagaggg tgacacggac     120
gctggcctga agctgaaga gcaggcatt ggagacaccc ccagcctgga agacgaagct       180
gctggtcacg tgacccaagc tcgcatggtc agtaaaagca agacgggac tggaagcgat      240 gacaaaaaag ccaaggggc tgatggtaaa acgaagatcg ccacaccgcg gggagcagcc     300
cctccaggcc agaagggcca ggccaacgcc accaggattc agcaaaaac cccgcccgct     360
```

-continued

```
ccaaagacac cacccagctc tggtgaacct ccaaaatcag gggatcgcag cggctacagc    420
agccccggct ccccaggcac tcccggcagc cgctcccgca ccccgtccct tccaacccca    480
cccacccggg agcccaagaa ggtggcagtg gtccgtactc cacccaagtc gccgtcttcc    540
gccaagagcc gcctgcagac agcccccgtg cccatgccag acctgaagaa tgtcacgtcc    600
aagatcggct ccactgagaa cctgaagcac cagccgggag gcgggaaggt gcagataatt    660
aataagctgg atcttagcaa cgtccagtcc aagtgtggct caaaggataa tatcaaacac    720
gtcctgggag gcggcagtgt gcaaatagtc tacaaaccag ttgacctgag caaggtgacc    780
tccaagtgtg gctcattagg caacatccat cataaaccag gaggtggcca gatggaagta    840
aaatctgaga agcttgactt caaggacaga gtccagtcga agattgggtc cctggacaat    900
atcacccacg tccctggcgg aggaaataaa aagattgaaa cccacaagct gaccttccgc    960
gagaacgcca agccaagac agaccacggg gcggagatcg tgtacaagtc gccagtggtg   1020
tctggggaca cgtctccatg gcatctcagc aatgtctcct ccaccggcag catcgacatg   1080
gtagactcgc cccagctcgc cacgctagct gacgaggtgt ctgcctccct ggccaagcag   1140
ggtttgtga                                                            1149
```

<210> SEQ ID NO 6
<211> LENGTH: 441
<212> TYPE: PRT
<213> ORGANISM: homo sapiens

<400> SEQUENCE: 6

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220
```

```
Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
        260                 265                 270

Gly Lys Val Gln Ile Ile Asn Lys Lys Leu Asp Leu Ser Asn Val Gln
    275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
        340                 345                 350

Lys Ile Gly Ser Leu Asp Asn Ile Thr His Val Pro Gly Gly Gly Asn
    355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
        420                 425                 430

Ser Ala Ser Leu Ala Lys Gln Gly Leu
    435                 440

<210> SEQ ID NO 7
<211> LENGTH: 1326
<212> TYPE: DNA
<213> ORGANISM: homo sapiens

<400> SEQUENCE: 7
atggctgagc ccgccagga gttcgaagtg atggaagatc acgctgggac gtacgggttg      60
ggggacagga agatcagggg gggctacacc atgcaccaag accaagaggg tgacacggac     120
gctggcctga agaatctccc cctgcagacc cccactgagg acggatctga ggaaccgggc     180
tctgaaacct ctgatgctaa gagcactcca acagcggaag atgtgacagc acccttagtg     240
gatgagggag ctcccggcaa gcaggctgcc gcgcagcccc acacggagat cccagaagga     300
accacagctg aagaagcagg cattggagac ccccagcc tggaagacga agctgctggt       360
cacgtgaccc aagctcgcat ggtcagtaaa agcaaagacg ggactggaag cgatgacaaa     420
aaagccaagg gggctgatgg taaaacgaag atcgccacac gcggggagc agcccctcca      480 ggccagaagg gccaggccaa cgccaccagg attccagcaa aaacccccgcc cgctccaaag    540 acaccaccca gctctggtga acctccaaaa tcagggatc gcagcggcta cagcagcccc     600
ggctccccag gcactcccgg cagccgctcc cgcaccccgt cccttccaac cccacccacc     660
cgggagccca gaaggtggc agtggtccgt actccaccca gtcgccgtc ttccgccaag       720 agccgcctgc agacagcccc cgtgcccatg ccagacctga gaatgtcaa gtccaagatc      780 ggctccactg agaacctgaa gcaccagccg ggaggcggga aggtgcagat aattaataag     840
aagctggatc ttagcaacgt ccagtccaag tgtggctcaa aggataatat caaacacgtc     900
```

-continued

```
ccgggaggcg gcagtgtgca aatagtctac aaaccagttg acctgagcaa ggtgacctcc    960
aagtgtggct cattaggcaa catccatcat aaaccaggag gtggccaggt ggaagtaaaa   1020
tctgagaagc ttgacttcaa ggacagagtc cagtcgaaga ttgggtccct ggacaatatc   1080
acccacgtcc ctggcggagg aaataaaaag attgaaaccc acaagctgac cttccgcgag   1140
aacgccaaag ccaagacaga ccacggggcg gagatcgtgt acaagtcgcc agtggtgtct   1200
ggggacacgt ctccacggca tctcagcaat gtctcctcca ccggcagcat cgacatggta   1260
gactcgcccc agctcgccac gctagctgac gaggtgtctg cctccctggc caagcagggt   1320
ttgtga                                                             1326
```

<210> SEQ ID NO 8
<211> LENGTH: 412
<212> TYPE: PRT
<213> ORGANISM: homo sapiens

<400> SEQUENCE: 8

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285
```

| | | | | | | | | | | | |
|---|---|---|---|---|---|---|---|---|---|---|---|
|Val|Thr|Ser|Lys|Cys|Gly|Ser|Leu|Gly|Asn|Ile|His His Lys Pro Gly|
| |290| | | |295| | | |300| | |

Gly Gly Gln Val Glu Val Lys Ser Glu Lys Leu Asp Phe Lys Asp Arg
305            310                315                320

Val Gln Ser Lys Ile Gly Ser Leu Asp Asn Ile Thr His Val Pro Gly
          325                330                335

Gly Gly Asn Lys Lys Ile Glu Thr His Lys Leu Thr Phe Arg Glu Asn
          340                345                350

Ala Lys Ala Lys Thr Asp His Gly Ala Glu Ile Val Tyr Lys Ser Pro
       355                360                365

Val Val Ser Gly Asp Thr Ser Pro Arg His Leu Ser Asn Val Ser Ser
       370                375                380

Thr Gly Ser Ile Asp Met Val Asp Ser Pro Gln Leu Ala Thr Leu Ala
385                390                395                400

Asp Glu Val Ser Ala Ser Leu Ala Lys Gln Gly Leu
              405                410

<210> SEQ ID NO 9
<211> LENGTH: 1239
<212> TYPE: DNA
<213> ORGANISM: homo sapiens

<400> SEQUENCE: 9

```
atggctgagc cccgccagga gttcgaagtg atggaagatc acgctgggac gtacggttg      60 ggggacagga agatcagggg gggctacacc atgcaccaag accaagaggg tgacacggac    120
gctggcctga agaatctccc cctgcagacc cccactgagg acggatctga ggaaccgggc    180
tctgaaacct ctgatgctaa gagcactcca acagcggaag ctgaagaagc aggcattgga    240 gacacccca gcctggaaga cgaagctgct ggtcacgtga cccaagctcg catggtcagt    300
aaaagcaaag acgggactgg aagcgatgac aaaaaagcca aggggctga tggtaaaacg    360 aagatcgcca caccgcgggg agcagcccct ccaggccaga agggccaggc caacgccacc    420
aggattccag caaaaacccc gcccgctcca agacaccac ccagctctgg tgaacctcca    480
aaatcagggg atcgcagcgg ctacagcagc cccggctccc caggcactcc cggcagccgc    540
tcccgcaccc cgtcccttcc aaccccaccc accggtgagc caagaaggt ggcagtggtc    600 cgtactccac ccaagtcgcc gtcttccgcc aagagccgcc tgcagacagc ccccgtgccc    660
atgccagacc tgaagaatgt caagtccaag atcggctcca ctgagaacct gaagcaccag    720
ccgggaggcg gaaggtgca gataattaat aagaagctgg atcttagcaa cgtccagtcc    780
aagtgtggct caaaggataa tatcaaacac gtcccgggag cggcagtgt gcaaatagtc    840 tacaaaccag ttgacctgag caaggtgacc tccaagtgtg gctcattagg caacatccat    900
cataaaccag gaggtggcca ggtggaagta aatctgaga agcttgactt caaggacaga    960
gtccagtcga agattgggtc cctggacaat atcacccacg tccctggcgg aggaaataaa   1020
aagattgaaa cccacaagct gaccttccgc gagaacgcca agccaagac agaccacggg   1080 gcggagatcg tgtacaagtc gccagtggtg tctggggaca cgtctccacg gcatctcagc   1140
aatgtctcct ccaccggcag catcgacatg gtagactcgc ccagctcgc cacgctagct   1200 gacgaggtgt ctgcctccct ggccaagcag ggtttgtga                          1239
```